United States Patent
Staehle et al.

(10) Patent No.: US 7,135,587 B2
(45) Date of Patent: Nov. 14, 2006

(54) UREA AND URETHANE DERIVATIVES AS INTEGRIN INHIBITORS

(75) Inventors: Wolfgang Staehle, Ingelheim (DE); Alfred Jonczyk, Darmstadt (DE); Oliver Schadt, Rodenbach (DE); Simon Goodman, Griesheim (DE)

(73) Assignee: Merck Patent GmbH, Darmstadt (DE)

( * ) Notice: Subject to any disclaimer, the term of this patent is extended or adjusted under 35 U.S.C. 154(b) by 233 days.

(21) Appl. No.: 10/450,855

(22) PCT Filed: Nov. 30, 2001

(86) PCT No.: PCT/EP01/14039

§ 371 (c)(1),
(2), (4) Date: Jun. 18, 2003

(87) PCT Pub. No.: WO02/50039

PCT Pub. Date: Jun. 27, 2002

(65) Prior Publication Data

US 2004/0063644 A1    Apr. 1, 2004

(30) Foreign Application Priority Data

Dec. 18, 2000  (DE) .............................. 100 63 173

(51) Int. Cl.
*C07C 229/00*  (2006.01)
(52) U.S. Cl. ............... 560/41; 560/19; 560/35; 560/155; 560/168; 560/169; 562/433; 562/553; 562/561; 564/123; 564/161; 564/163; 564/169; 564/225; 564/244

(58) Field of Classification Search ................ 564/225, 564/226, 227, 230, 233, 234, 235, 236, 237, 564/238, 240, 248, 114, 123; 562/433, 455, 562/456, 442, 440
See application file for complete search history.

(56) References Cited

U.S. PATENT DOCUMENTS 6,645,991 B1 * 11/2003 Jonczyk et al. ............. 514/352

FOREIGN PATENT DOCUMENTS

| WO | WO 9622966 A | 8/1996 |
| WO | WO 9952493 A | 10/1999 |
| WO | WO 0064866 A | 11/2000 |

* cited by examiner

*Primary Examiner*—Johann Richter
*Assistant Examiner*—Karl Puttlitz
(74) *Attorney, Agent, or Firm*—Millen, White, Zelano, Branigan, P.C.

(57) ABSTRACT

Novel urea and urethane derivatives of general formula (I) in which R1, R2, R3, R5, R5', X, Y, B, m, n and o are as defined in Patent Claim 1, and physiologically acceptable salts or solvates thereof are integrin inhibitors and can be employed for combating thromboses, cardiac infarction, coronary heart disease, arteriosclerosis, inflammation, tumors. Osteoporosis, infections and restenosis after angioplasty or in pathological processes maintained or propagated by antiogenesis.

18 Claims, No Drawings

UREA AND URETHANE DERIVATIVES AS INTEGRIN INHIBITORS

The invention relates to urea and/or urethane derivatives of the formula I

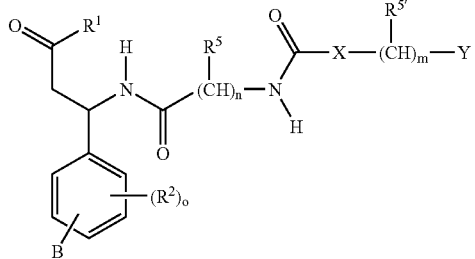

in which

| | |
|---|---|
| X | is O or $NR^5$, |
| Y | is $-N(R^5)R^4$, $-C(=NR^7)-NHR^7$ or $-C(=NR^9)-NHR^7$, |
| B | is H or ![phenyl-(R³)p] |
| R | is H, A, cycloalkyl, Ar, arylalkyl or Pol, |
| $R^1$ | is OR or $N(R)_2$, |
| $R^2$ and $R^3$ | are each, independently of one another, H, A, Hal, $NO_2$, OR, $N(R)_2$, CN, CO—R, $SO_3R$, $SO_2R$, NH—C(O)A or SR, |
| $R^4$ | is H, $R^7$, $-C(=NR^7)-NHR^7$, $-C(=NR^9)-NHR^7$, $-C(=CH-NO_2)-NHR^7$ or Het, |
| $R^5$ and $R^{5'}$ | are each, independently of one another, H or A, |
| $R^6$ | is Hal or $NO_2$, |
| $R^7$ | is H, $-C(O)R^8$, $-C(O)-Ar$, $R^8$, $COOR^8$, $COO-(CH_2)_o-Ar$, $SO_2-Ar$, $SO_2R^8$ or $SO_2$-Het, |
| $R^8$ | is A or cycloalkyl, |
| $R^9$ | is CN or $NO_2$, |
| A | is alkyl having 1 to 8 carbon atoms, where the alkyl groups may be monosubstituted or polysubstituted by $R^6$ and/or their alkyl carbon chain may be interrupted by —O—, |
| Ar | is phenyl, naphthyl, anthryl or biphenylyl, each of which is unsubstituted or monosubstituted, disubstituted or trisubstituted by A, OH, OA, CN, $NO_2$ or Hal, |
| cycloalkyl | is cycloalkyl having from 3 to 15 carbon atoms, |
| Hal | is F, Cl, Br or I, |
| Het | is a saturated, partially unsaturated or fully unsaturated monocyclic or bicyclic heterocyclic radical having from 5 to 10 ring members, where 1 or 2 N and/or 1 or 2 S or O atoms may be present, and the heterocyclic radical may be monosubstituted or disubstituted by =O, A, $NO_2$, NHCOA or NHA, |
| Pol | is a solid phase with no terminal functional group, |
| n and m | are each, independently of one another, 1, 2, 3, 4, 5 or 6, |
| o | is 1, 2, 3 or 4, |
| p | is 1, 2, 3, 4 or 5, |

Partially similar compounds are disclosed in WO 97/26250.

The object of the invention was to discover novel compounds having valuable properties, in particular those which are used for the preparation of medicaments.

It has been found that the compounds of the formula I and their salts are well tolerated and have very valuable pharmacological properties. In particular, they act as integrin inhibitors, inhibiting, in particular, the interactions of the αvβ3 or αvβ6 integrin receptors with ligands. Integrins are membrane-bound, heterodimeric glycoproteins consisting of an α subunit and a smaller β subunit. The relative affinity and specificity for ligand binding is determined by recombination of the various α and β subunits. Particular efficacy is exhibited by the compounds according to the invention in the case of integrins αvβ1, αvβ3, αvβ5, αIIbβ3, αvβ6 and αvβ8, preferably αvβ3, αvβ5 and αvβ6. In particular, potent selective inhibitors of integrin αvβ3 and αvβ6, very particularly potent selective inhibitors of Integrin αvβ6, have been found. αvβ3 integrin is expressed in a number of cells, for example endothelium cells, cells of smooth vascular muscles, for example the aorta, cells for breaking down bone matrix (osteoclasts) or tumour cells.

The action of the compounds according to the invention can be demonstrated, for example, by the method described by J. W. Smith et al. in J. Biol. Chem. 1990, 265, 12267–12271.

The dependence of formation of angiogenesis on the interaction between vascular integrins and extracellular matrix proteins has been described by P. C. Brooks, R. A. Clark and D. A. Cheresh in Science 1994, 264, 569–571.

The possibility of inhibiting this interaction and so initiating apoptosis (programmed cell death) of angiogenic vascular cells by a cyclic peptide has been described by P. C. Brooks, A. M. Montgomery, M. Rosenfeld, R. A. Reisfeld, T. Hu, G. Klier and D. A. Cheresh in Cell 1994, 79, 1157–1164. In this, for example, αvβ3 antagonists or antibodies against αvβ3 were described which cause shrinkage of tumours due to the initiation of apoptosis.

The experimental evidence that the compounds according to the invention also prevent the attachment of living cells to the corresponding matrix proteins and accordingly also prevent the attachment of tumour cells to matrix proteins can be provided in a cell adhesion test analogously to the method of F. Mitjans et al., J. Cell Science 1995, 108, 2825–2838.

The compounds of the formula I are able to inhibit the binding of metalloproteinases to integrins and thus prevent the cells utilising the enzymatic activity of the proteinase. An example can be found in the ability of a cyclo-RGD peptide to inhibit the binding of MMP-2 (matrix-metalloproteinase-2) to the vitronectin receptor αvβ3, as described in P. C. Brooks et al., Cell 1996, 85, 683–693.

Compounds of the formula I which block the interaction of integrin receptors and ligands, such as, for example, of fibrinogen to the fibrinogen receptor (glycoprotein IIb/IIIa), prevent, as antagonists, the spread of tumour cells by metastasis and can therefore be employed as antimetastatic substances in operations in which tumours are removed or attacked surgically. This is confirmed by the following observations:

The spread of tumour cells from a local tumour into the vascular system occurs through the formation of microaggregates (microthromboses) due to the interaction of the tumour cells with blood platelets. The tumour cells are masked by the protection in the microaggregate and are not recognised by the immune system cells. The microaggregates are able to attach to vessel walls, simplifying further penetration of tumour cells into the tissue. Since the formation of microthromboses is promoted by ligand binding to the corresponding integrin receptors, for example αvβ3 or αIIbβ3, on activated blood platelets, the corresponding antagonists can be regarded as effective metastasis inhibitors.

The action of a compound on an αvβ5 integrin receptor and thus the activity as an inhibitor can be demonstrated, for example, by the method described by J. W. Smith et al. in J. Biol. Chem. 1990, 265, 12267–12271.

The compounds of the formula I can be employed as medicament active ingredients in human and veterinary medicine, in particular for the prophylaxis and/or therapy of circulation disorders, thromboses, cardiac infarction, arteriosclerosis, apoplexia, angina pectoris, tumour diseases, such as tumour development or tumour metastasis, osteolytic diseases, such as osteoporosis, pathologically angiogenic diseases, such as, for example, inflammations, opthalmological diseases, diabetic retinopathy, macular degeneration, myopia, ocular histoplasmosis, rheumatic arthritis, osteo-arthritis, rubeotic glaucoma, ulcerative colitis, Crohn's disease, atherosclerosis, psoriasis, restenosis after angioplasty, multiple sclerosis, viral infection, bacterial infection, fungal infection, in acute kidney failure and in wound healing for supporting the healing process.

αvβ6 is a relatively rare integrin (Busk et al., 1992 J. Biol. Chem. 267(9), 5790) which is increasingly formed in repair processes in epithelial tissue and which preferentially binds the natural matrix molecules fibronectin and tenascin (Wang et al., 1996, Am. J. Respir. Cell Mol. Biol. 15(5), 664). The physiological and pathological functions of αvβ6 are not yet known precisely, but it is assumed that this integrin plays an important role in physiological processes and illnesses (for example inflammation, wound healing, tumours) in which epithelial cells are involved. Thus, αvβ6 is expressed on keratinocytes in wounds (Haapasalmi et al., 1996, J. Invest. Dermatol. 106(1), 42), from which it can be assumed that, besides wound-healing processes and inflammation, other pathological events in the skin, such as, for example, psoriasis, can also be influenced by agonists or antagonists of the said integrin. Furthermore, αvβ6 plays a role in the respiratory tract epithelium (Weinacker et al., 1995, Am. J. Respir. Cell Mol. Biol. 12(5), 547), and consequently corresponding agonists/antagonists of this integrin could successfully be employed in respiratory tract illnesses, such as bronchitis, asthma, lung fibrosis and respiratory tract tumours. Finally, it is known that αvβ6 also plays a role in the intestinal epithelium, which means that the corresponding integrin agonists/antagonists could be used in the treatment of inflammation, tumours and wounds of the gastric/intestinal tract.

The action of a compound on an αvβ6 integrin receptor and thus the activity as an inhibitor can be demonstrated, for example, by the method described by J. W. Smith et al. in J. Biol. Chem. 1990, 265, 12267–12271.

The compounds of the formula I can be employed as antimicrobial substances in operations where biological materials, implants, catheters or cardiac pacemakers are used. They have an antiseptic action here. The efficacy of the antimicrobial activity can be demonstrated by the method described by P. Valentin-Weigund et al. in Infection and Immunity, 1988, 2851–2855.

A measure of the uptake of a medicament active ingredient in an organism is its bioavailability.

If the medicament active ingredient is administered to the organism intravenously in the form of an injection solution, its absolute bioavailability, i.e. the proportion of the pharmaceutical species which is unchanged in the systemic blood, i.e. enters the general circulation, is 100%.

On oral administration of a therapeutic active ingredient, the active ingredient is generally in the form of a solid in the formulation and must therefore first dissolve in order that it can overcome the entry barriers, for example the gastrointestinal tract, the oral mucous membrane, nasal membranes or the skin, in particular the stratum corneum, and can be absorbed by the body. Pharmacokinetic data, i.e. on the bioavailability, can be obtained analogously to the method of J. Shaffer et al., J. Pharm. Sciences, 1999, 88, 313–318. A further measure of the absorbability of a therapeutic active ingredient is the logD value, since this value is a measure of the lipophilicity of a molecule.

The compounds of the formula I have at least one centre of chirality and can therefore occur in a number of stereoisomeric forms. All of these forms (for example R- and S-enantiomers) and diastereomers (for example RR-, RS-, SR- or SS-forms in the case of compounds having two stereocentres) are included in the formula.

The compounds according to the invention according to Claim 1 also cover so-called prodrug derivatives, i.e. compounds of the formula I modified with, for example, alkyl or acyl groups, sugars or oligopeptides, which are rapidly cleaved in the organism to give the effective compounds according to the invention.

Furthermore, free amino groups or free hydroxyl groups can be provided as substituents of compounds of the formula I with corresponding protecting groups.

The term solvates of the compounds of the formula I is taken to mean adductions of inert solvent molecules onto the compounds of the formula I which form owing to their mutual attractive force. Solvates are, for example, mono- or dihydrates or addition compounds with alcohols, such as, for example, with methanol or ethanol.

The invention relates to the compounds of the formula I and their salts and solvates according to Claim 1 and to a process for the preparation of compounds of the formula I and their salts and solvates, characterised in that (a) a compound of the formula II

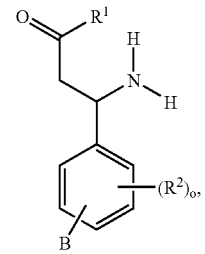

II in which B, R, $R^1$, $R^2$, $R^3$, o and p are as defined in Claim 1, but R≠H, and in which free hydroxyl or amino groups as substituents $R^2$ or $R^3$ are protected by protecting groups, is reacted with a compound of the formula III

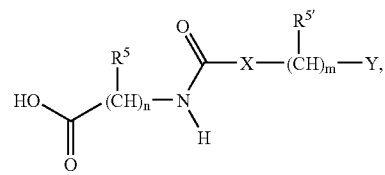

III in which X, Y, $R^5$, $R^{5'}$, n and m are as defined in Claim 1, and, if desired, the radical R≠H is converted into the radical R=H, and any protecting groups on $R^2$ and/or $R^3$ are removed, or (b) a compound of the formula IV

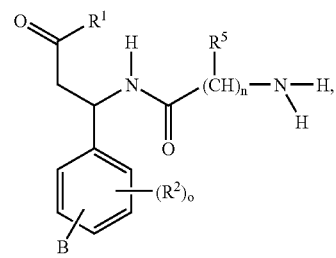

IV in which B, R, $R^1$, $R^2$, $R^3$, $R^5$, n, o and p are as defined in Claim 1, but R≠H, and in which free hydroxyl or amino groups as substituents $R^2$ or $R^3$ are protected by protecting groups, is reacted with a compound of the formula V

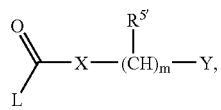

in which X, Y, R$^{5'}$ and m are as defined in Claim 1, and L is Cl, Br, OH or a reactive, esterified OH group, and, if desired, the radical R≠H is converted into the radical R═H, and any protecting groups on R$^2$ and/or R$^3$ are removed, or (c) in a compound of the formula I, one or more radicals R, R$^1$, R$^2$, R$^3$, R$^4$ and/or R$^5$ are converted into one or more radicals R, R$^1$, R$^2$, R$^3$, R$^4$ and/or R$^5$ by, for example,
   i) alkylating a hydroxyl group,
   ii) hydrolysing an ester group to a carboxyl group,
   iii) esterifying a carboxyl group,
   iv) alkylating an amino group,
   v) reacting an aryl bromide or iodide with boronic acids by a Suzuki coupling to give the corresponding coupling products, or
   vi) acylating an amino group, and/or a basic or acidic compound of the formula I is converted into one of its salts or solvates by treatment with an acid or base.

Above and below, the radicals R$^1$ to R$^9$, R$^{5'}$, B, X and Y are as defined under the stated formulae, unless expressly stated otherwise. In particular, radicals listed more than once, for example R$^5$, can have different meanings corresponding to the definition.

In the above formulae, A is alkyl, is linear or branched, and has from 1 to 8, preferably 1, 2, 3, 4, 5 or 6 carbon atoms. A is preferably methyl, furthermore ethyl, n-propyl, isopropyl, n-butyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, heptyl or octyl. Further preferred embodiments of A are the said alkyl groups, which, however, may be monosubstituted or polysubstituted by Hal or NO$_2$, preferably trifluoromethyl, 2,2,2-trifluoroethyl or 2-nitroethyl, or alkyl groups, whose carbon chain may be interrupted by —O—, preferably —CH$_2$—O—CH$_3$, —CH$_2$—O—CH$_2$—CH$_3$ or —CH$_2$—CH$_2$—O—CH$_3$.

A is particularly preferably methyl, ethyl or trifluoromethyl. A is very particularly preferably methyl or ethyl.

Ar is aryl which is unsubstituted or monosubstituted, disubstituted or trisubstituted by A, OH, OA, CN, NO$_2$ or Hal, where aryl is phenyl, naphthyl, anthryl or biphenylyl. Ar is preferably phenyl or naphthyl which is unsubstituted or monosubstituted, disubstituted or trisubstituted by A, OH, OA, CN, NO$_2$ or Hal. Ar is particularly preferably phenyl.

Arylalkyl is also —(CH$_2$)$_x$—Ar, where Ar has one of the preferred meanings indicated above and where x may be 1, 2 or 3, arylalkyl is preferably benzyl, phenylethyl or phenylpropyl; arylalkyl is particularly preferably benzyl.

Cycloalkyl having from 3 to 15 carbon atoms is preferably cyclopropyl, cyclobutyl, cyclopentyl, cyclohexyl, cycloheptyl or cyclooctyl, cycloalkyl is likewise a monocyclic or bicyclic terpene, preferably p-menthane, menthol, pinane, bornane or camphor, where each known stereoisomeric form is included, or adamantyl. For camphor, this is both L-camphor and D-camphor.

Hal is preferably F, Cl or bromine. Hal is particularly preferably Cl.

Het is a saturated, partially unsaturated or fully unsaturated monocyclic or bicyclic heterocyclic radical having from 5 to 10 ring members, where 1 or 2 N and/or 1 or 2 S or O atoms may be present, and which may be monosubstituted or disubstituted by ═O, A, NO$_2$, NHCOA or NHA.

Het is preferably substituted or unsubstituted 2- or 3-furyl, 2- or 3-thienyl, 1-, 2- or 3-pyrrolyl, 1-, 2-, 4- or 5-imidazolyl, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -4 or -5-yl, 1- or 5-tetrazolyl, 1,2,3-oxadiazol-4- or -5-yl 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6- or 7-benzofuryl, 2- 3-, 4-, 5-, 6- or 7-benzothienyl, 1-, 2-, 3-, 4-, 5-, 6- or 7-1H-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 4- or 5-benzothiadiazolyl, 2-, 4-, 5-, 6- or 7-benzisothiazolyl, 4-, 5-, 6- or 7-benz-2,1,3-oxadiazolyl, 1-, 2-, 3-, 4-, 5-, 6-, 7- or 8-quinolinyl, 1-, 3-, 4-, 5-, 6-, 7- or 8-isoquinolinyl, 1-, 2-, 3-, 4- or 9-carbazolyl, 1-, 2-, 3-, 4-, 5-, 6-, 7-, 8- or 9-acridinyl, 3-, 4-, 5-, 6-, 7- or 8-cinnolinyl, 2-, 4-, 5-, 6-, 7- or 8-quinazolinyl. The heterocyclic radicals may also be partially or fully hydrogenated. Het can thus also be 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -3-pyrrolyl, tetrahydro-1-, -2- or 4-imidazolyl, 2,3-dihydro-1-, -2-, -3-, -4-, -5-, -6- or -7-1H-indolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1,2,3,6-tetrahydro-1-, -2-, -3,-4-, -5- or -6-pyridyl, 1-, 2-, 3- or 4-piperidinyl, 1-, 2-, 3- or 4-azepanyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolinyl, 1,2,3,4-tetrahydro-1-, -2-, -3-, -4-, -5-, -6-, -7- or -8-isoquinolinyl.

The said heterocyclic rings may also be monosubstituted or disubstituted by ═O, A, NO$_2$, NHCOA or NHA.

Het is preferably 3-nitropyridin-2-yl, 6-methylpyridin-2-yl. 3-aminopyridin-2-yl, 3-(N-acetylamino)pyridin-2-yl, pyridin-2-yl, 1,4,5.6-tetrahydropyridin-2-yl, benzimidazol-2-yl, imidazol-2-yl, 4,5-dihydroimidazol-2-yl, 3,5-dihydroimidazol-4-on-2-yl, pyrimidin-2-yl, quinazolin-2-yl or 1,4, 5,6-tetrahydro-pyrimidin-2-yl. Het is particularly preferably pyridin-2-yl or benzimidazol-2-yl. Het is very particularly preferably pyridin-2-yl.

Pol is a solid phase with no terminal functional group, as explained in greater detail below. The terms solid phase and resin are used synonymously below.

In compounds of the formula I in which B≠H, the second phenyl radical is preferably coupled to the first phenyl radical in the 3- or 4-position, particularly preferably to the 4-position of the first phenyl ring.

X is O or NR⁵, where R⁵ has one of the meanings described below.

Y is —N(R⁵)R⁴, —C(=NR⁷)—NHR⁷ or —C(=NR⁹)—NHR⁷, where R⁴, R⁵, R⁷ and R⁹ have one of the meanings described below. Y is particularly preferably the —N(R⁵)R⁴ group.

B is H or

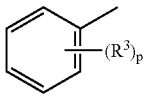

where R³ and p have one of the meanings given below.

R¹ is OR or N(R)₂, where R has one of the meanings below. R¹ is preferably OR.

R is H, A, cycloalkyl, Ar, arylalkyl or Pol, where A, cycloalkyl, Ar and arylalkyl have one of the meanings described above, and Pol has one of the meanings described below. R is preferably A, Pol or H. R is particularly preferably H or A. R is very particularly preferably H.

Compounds of the formula I in which OR is OPol are in other words polymer-bound compounds of the formula I, in which the acid function is bound to a polymeric support. The polymer-bound compounds of the formula I are intermediates in the synthesis of the free acids of the formula I or salts or hydrates thereof.

R² and R³ are each, independently of one another, H, A, Hal, NO₂, OR, N(R)₂, CN, CO—R, SO₃R, SO₂R, NH—C(O)A or SR, where A and R have one of the meanings described above. R² is particularly preferably H or Hal. R² is very particularly preferably Hal, and o=2 if B is H. R² is very particularly preferably H if B is

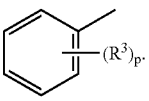

R³ is particularly preferably H, A, Hal, OA or CN, where Hal is particularly preferably F and/or Cl, R³ is very particularly preferably H or Hal.

R⁴ is H, R⁷, —C(=NR⁷)—NHR⁷, —C(=NR⁹)—NHR⁷ or Het, where Het has one of the meanings indicated above, and R⁷ and R⁹ have one of the meanings given below. R⁴ is preferably Het.

R⁵ is H or A, where A has one of the meanings given above. R⁵ is particularly preferably H.

R⁵' is H or A, where A has one of the meanings given above. R⁵' is particularly preferably H.

R⁶ is Hal or NO₂, where Hal has one of the meanings given above. R⁶ is particularly preferably Hal.

R⁷ is preferably H, —C(O)R⁸, —C(O)—Ar, R⁸, COOR⁸, COO—(CH₂)ₒ—Ar, SO₂—Ar, SO₂R⁸ or SO₂-Het, where Ar and Het have one of the meanings indicated above, and R⁸ is alkyl having from 1 to 10 carbon atoms or cycloalkyl having from 3 to 15 carbon atoms. R⁷ is preferably H, methoxycarbonyl, ethoxycarbonyl, tert-butoxycarbonyl or benzyloxycarbonyl.

R⁸ is alkyl having from 1 to 10 carbon atoms or cycloalkyl having from 3 to 15 carbon atoms, where the terms alkyl and cycloalkyl have one of the meanings described above. R⁷ is preferably tert-butyl, 2,2-dimethylpropyl, cyclopropyl or cyclohexyl.

R⁹ is CN or NO₂, particularly preferably CN.

m and n are each, independently of one another, 1, 2, 3, 4, 5 or 6. m is particularly preferably 2, 3 or 4. m is very particularly preferably 2.

n is preferably 1 or 2. n is particularly preferably 1.

o is 1, 2, 3 or 4, particularly preferably 1.

p is 1, 2, 3, 4 or 5, particularly preferably 1 or 2, very particularly preferably 1.

Accordingly, the invention relates in particular to the compounds of the formula I in which at least one of the said radicals has one of the preferred meanings indicated above. Some preferred groups of compounds may be expressed by the following sub-formulae Ia to In, which conform to the formula I and in which the radicals not designated in greater detail have the meaning indicated under the formula I, but in which

| | | |
|---|---|---|
| in Ia | R¹ | is OR, |
| in Ib | R¹ | is OR and |
| | R | is H or A, |
| in Ic | R¹ | is OR and |
| | R | is Pol, |
| in Id | R¹ | is OR and |
| | X | is O, |
| in Ie | R¹ | is OR and |
| | X | is NR⁵, |
| in If | R¹ | is OR, |
| | R | is H or A, |
| | B | is H, |
| | X | is O, |
| | Y | is —N(R⁵)R⁴, |
| | R⁴ | is Het, |
| | R⁵ in —N(R⁵)R⁴ | is H, |
| | m | is 2 or 3, |
| | n | is 1; |
| in Ig | R¹ | is OR, |
| | R | is H, |
| | B | is H, |
| | R² | is Hal, |
| | X | is O, |
| | Y | is —N(R⁵)R⁴, |
| | R⁴ | is Het, |
| | R⁵ in —N(R⁵)R⁴ | is H, |
| | o | is 2, |
| | m | is 2, |
| | n | is 1: |
| in Ih | R¹ | is OR, |
| | R | is H or A, |
| | B | is   |
| | X | is O, |
| | Y | is —N(R⁵)R⁴, |
| | R⁴ | is Het, |
| | R⁵ in —N(R⁵)R⁴ | is H, |
| | m | is 2 or 3, |
| | n | is 1; |
| in Ii | R¹ | is OR, |
| | R | is H or A, |
| | X | is O, |
| | R² | is H, |
| | R³ | is Hal or A, |
| | Hal | is Cl or F, |
| | Y | is —N(R⁵)R⁴, |
| | R⁴ | is Het, |
| | Het | is pyridin-2-yl, |
| | R⁵ in —N(R⁵)R⁴ | is H, |
| | m | is 2, |
| | n | is 1, |
| | o | is 1 and |
| | p | is 1 or 2; |

-continued

| | | |
|---|---|---|
| in Ij | $R^1$ | is OR, |
| | R | is H or A, |
| | X | is O, |
| | $R^2$ | is H, |
| | $R^3$ | is H, |
| | Y | is —$N(R^5)R^4$, |
| | $R^4$ | is Het, |
| | Het | is pyridin-2-yl or benzimidazol-2-yl, |
| | $R^5$ in —$N(R^5)R^4$ | is H, |
| | m | is 2 or 3, |
| | n | is 1, |
| | o | is 1; |
| in Ik | $R^1$ | is OR, |
| | R | is H or A, |
| | B | is H, |
| | X | is $NR^5$, |
| | Y | is —$N(R^5)R^4$, |
| | $R^4$ | is Het, |
| | $R^5$ | is H, |
| | m | is 2, 3 or 4, |
| | n | is 1; |
| in Im | $R^1$ | is OR, |
| | R | is H or A, |
| | B | is ₚ, |
| | X | is $NR^5$, |
| | Y | is —$N(R^5)R^4$, |
| | $R^4$ | is Het, |
| | $R^5$ | is H, |
| | m | is 2, 3 or 4, |
| | n | is 1; |
| in In | $R^1$ | is OR, |
| | R | is H or A, |
| | X | is $NR^5$, |
| | $R^2$ | is H, |
| | $R^3$ | is H or Hal, |
| | Hal in $R^3$ | is Cl, |
| | Y | is —$N(R^5)R^4$, |
| | $R^4$ | is pyridin-2-yl or benzimidazol-2-yl, |
| | $R^5$ | is H, |
| | m | is 2, 3 or 4, |
| | n | is 1, |
| | o | is 1 and |
| | p | is 1. |

Preferred compounds of the formula I are a) 3-biphenyl-4-yl-3-{2-[3-(pyridin-2-ylamino)propoxycarbonylamino]ethanoylamino}propionic acid,
b) 3-biphenyl-4-yl-3-{2-[3-(pyridin-2-ylamino)ethoxycarbonylamino]ethanoyl-amino}propionic acid,
c) 3-(3'-chlorobiphenyl-4-yl)-3-{2-[2-(pyridin-2-ylamino)ethoxycarbonylamino]ethanoylamino}propionic acid,
d) 3-(4'-chlorobiphenyl-4-yl)-3-{2-[2-(pyridin-2-ylamino)ethoxycarbonylamino]ethanoylamino}propionic acid,
e) 3-(3'-fluorobiphenyl-4-yl)-3-{2-[2-(pyridin-2-ylamino)ethoxycarbonylamino]ethanoylamino}propionic acid,
f) 3-(2'-fluorobiphenyl-4-yl)-3-{2-[2-(pyridin-2-ylamino)ethoxycarbonylamino]ethanoylamino}propionic acid,
g) 3-(4'-methylbiphenyl-4-yl)-3-{2-[2-(pyridin-2-ylamino)ethoxycarbonylamino]ethanoylamino}propionic acid,
h) 3-(3'-chloro-4'-fluorobiphenyl-4-yl)-3-{2-[2-(pyridin-2-ylamino)ethoxycarbonylamino]ethanoylamino}propionic acid,
i) 3-{2-[2-(pyridin-2-ylamino)ethoxycarbonylamino]ethanoylamino}-3-(4'-trifluoromethylbiphenyl-4-yl)propionic acid,
j) 3-{2-[2-(1H-benzimidazol-2-ylamino)ethoxycarbonylamino]ethanoyl-amino}-3-biphenyl-4-ylpropionic acid,
k) (3R)-3-biphenyl-4-yl-3-{2-[2-(pyridin-2-ylamino)ethoxycarbonylamino]ethanoylamino}propionic acid,
l) methyl 3-biphenyl-4-yl-3-{2-[2-(pyridin-2-ylamino)ethoxycarbonylamino]ethanoylamino}propionate,
m) 3-(3,5-dichlorophenyl)-3-{2-[2-(pyridin-2-ylamino)ethoxycarbonylamino]ethanoylamino}propionic acid,
n) 3-biphenyl-4-yl-3-(2-{3-[3-(pyridin-2-ylamino)propyl]ureido}ethanoylamino)propionic acid,
o) 3-(2-{3-[2-(1H-benzimidazol-2-ylamino)ethyl]ureido}ethanoylamino)-3-biphenyl-4-ylpropionic acid,
p) 3-biphenyl-4-yl-3-(2-{3-[2-(pyridin-2-ylamino)ethyl]ureido}ethanoylamino)propionic acid,
q) 3-(4'-chlorobiphenyl-4-yl)-3-(2-{3-[3-(pyridin-2-ylamino)propyl]ureido}ethanoylamino)propionic acid,
r) 3-(2-{3-[3-(1H-benzimidazol-2-ylamino)propyl]ureido}ethanoylamino)-3-biphenyl-4-ylpropionic acid and physiologically acceptable salts and solvates thereof.

The compounds of the formula I according to Claim 1 and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for said reactions. Use can also be made here of variants which are known per se, but are not mentioned here in greater detail.

If desired, the starting materials can also be formed in situ, so that they are not isolated from the reaction mixture, but are instead immediately converted further into the compounds of the formula I according to Claim 1.

It is also possible for a plurality of—identical or different—protected amino and/or hydroxyl groups to be present in the molecule of the starting material. If the protecting groups present differ from one another, they can in many cases be removed selectively (cf. in this respect: T. W. Greene, P. G. M. Wuts, Protective Groups in Organic Chemistry, 2nd Edn., Wiley, N.Y. 1991 or P. J. Kocienski, Protecting Groups, 1st Edn., Georg Thieme Verlag, Stuttgart-New-York, 1994).

The term "amino protecting group" is generally known and relates to groups which are suitable for protecting (blocking) an amino group against chemical reactions. Typical of such groups are, in particular, unsubstituted or substituted acyl, aryl, aralkoxymethyl or aralkyl groups. Since the amino protecting groups are removed after the desired reaction (or synthesis sequence), their type and size is furthermore not crucial; however, preference is given to those having 1–20, in particular 1–8 carbon atoms. The term "acyl group" is to be understood in the broadest sense in connection with the present process. It includes acyl groups derived aliphatic, araliphatic, alicyclic, aromatic and heterocyclic carboxylic acids or sulfonic acids, as well as, in particular, alkoxycarbonyl, alkenyloxycarbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as phenoxyacetyl; alkoxycarbonyl, such as methoxycarbonyl, ethoxycarbonyl, 2,2,2-trichloroethoxycarbonyl, BOC and 2-iodoethoxycarbonyl; alkenyloxy-carbonyl, such as allyloxycarbonyl (Aloc), aralkoxycarbonyl, such as CBZ (synonymous with Z), 4-methoxybenzyloxycarbonyl (MOZ), 4-nitrobenzyloxycarbonyl and 9-fluorenylmethoxycarbonyl (Fmoc); 2-(phenylsulfonyl)ethoxycarbonyl; trimethylsilylethoxycarbonyl (Teoc), and arylsulfonyl, such as 4-methoxy-2,3,6-trimethylphenylsulfonyl (Mtr). Preferred amino protecting groups are BOC, Fmoc and Aloc, furthermore CBZ, benzyl and acetyl. Particularly preferred protecting groups are BOC and Fmoc.

The term "hydroxyl protecting group" is likewise generally known and relates to groups which are suitable for protecting a hydroxyl group against chemical reactions. Typical of such groups are the above-mentioned unsubstituted or substituted aryl, aralkyl, aroyl or acyl groups, furthermore also alkyl groups, alkyl-, aryl- and aralkylsilyl groups, and O,O— and O,S-acetals. The nature and size of the hydroxyl protecting groups is not crucial since they are removed again after the desired chemical reaction or synthesis sequence; preference is given to groups having 1–20 carbon atoms, in particular 1–10 carbon atoms. Examples of hydroxyl protecting groups are, inter alia, aralkyl groups, such as benzyl, 4-methoxybenzyl and 2,4-di-methoxybenzyl, aroyl groups, such as benzoyl and p-nitrobenzoyl, acyl groups, such as acetyl and pivaloyl, p-toluenesulfonyl, alkyl groups, such as methyl and tert-butyl, but also allyl, alkylsilyl groups, such as trimethylsilyl (TMS), triisopropylsilyl (TIPS), tert-butyldimethylsilyl (TBS) and triethylsilyl, trimethylsilylethyl, aralkylsilyl groups, such as tert-butyldiphenylsilyl (TBDPS), cyclic acetals, such as isopropylidene acetal, cyclopentylidene acetal, cyclohexylidene acetal, benzylidene acetal, p-methoxybenzylidene acetal and o,p-dimethoxybenzylidene acetal, acyclic acetals, such as tetrahydropyranyl (Thp), methoxymethyl (MOM), methoxyethoxymethyl (MEM), benzyloxymethyl (BOM) and methylthiomethyl (MTM). Particularly preferred hydroxyl protecting groups are benzyl, acetyl, tert-butyl and TBS.

The liberation of the compounds of the formula I from their functional derivatives is known from the literature for the protecting group used in each case (for example T. W. Greene, P. G. M. Wuts, *Protective Groups in Organic Chemistry*, 2nd Edn., Wiley, N.Y. 1991 or P. J. Kocienski, *Protecting Groups*, 1st Edn., Georg Thieme Verlag, Stuttgart-N.Y., 1994). Use may also be made here of variants which are known per se, but are not mentioned here in greater detail.

The groups BOC and O-tert-butyl may, for example, be removed preferentially using TFA in dichloromethane or using approximately 3 to 5N HCl in dioxane at 15–30° C., and the Fmoc group using an approximately 5 to 50% solution of dimethylamine, diethylamine or piperidine in DMF at 15–30° C. The Aloc group can be removed under gentle conditions with noble-metal catalysis in chloroform at 20–30° C. A preferred catalyst is tetrakis(triphenylphosphine)palladium(0).

The starting compounds of the formulae II to V and 1 to 8 are generally known. If they are novel, however, they can be prepared by methods known per se.

The compounds of the formula I can also be synthesised on a solid phase, the binding to the solid phase taking place to $R^1$. In the case of synthesis on a solid phase, $R^1$ is likewise OPol, NHPol or NRPol, where Pol is a solid phase without a terminal functional group. Pol represents the polymeric support material and all atoms of the anchor group of a solid phase apart from the terminal functional group. The anchor groups of a solid phase, also known as linkers, are necessary for binding of the compound to be functionalised to the solid phase. A review of syntheses on the solid phase and the solid phases and/or linkers which can be employed for this purpose is given, for example, in Novabiochem—The Combinatorial Chemistry Catalog, March 99, pages S1–S72.

Particularly suitable solid phases for the synthesis of compounds according to the invention with $R^1$=OR are solid phases having a hydroxyl group as terminal functionality, for example Wang resin or polystyrene A OH. Particularly suitable solid phases for the synthesis of compounds according to the invention with $R^1$=N(R)$_2$ are solid phases having an amino group as terminal functionality, for example Rink amide resin.

Compounds of the formula II with $R^1$=OL, where L is Pol or R,

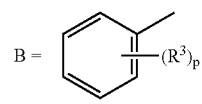

and R≠H (formula II-1), are prepared, for example, in accordance with the following reaction scheme 1, where SG$_1$ denotes an amino-protecting group, as described above.

Reaction scheme 1:

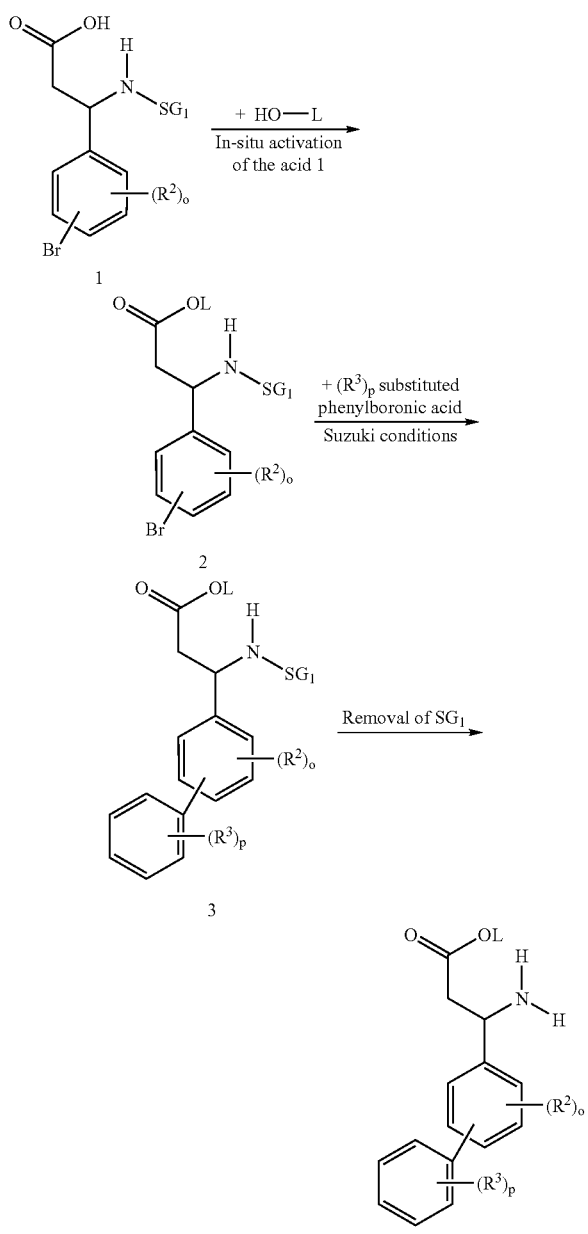

The bromophenyl-substituted carboxylic acid 1 is activated in situ by known methods, for example by reaction with diisopropylcarbodiimide, and reacted with the alcohol HO-L, where L is as defined above. The subsequent coupling of compound 2 to an ($R^3$)-substituted phenylboronic acid under Suzuki conditions generates the biphenyl derivative 3. The removal of the protecting group $SG_1$ under known conditions liberates a compound of the formula II-1.

The Suzuki reaction is advantageously carried out with palladium control, preferably by addition of $Pd(PPh_3)_4$, in the presence of a base, such as potassium carbonate, in an inert solvent or solvent mixture, for example DMF, at temperatures between 0° and 150°, preferably between 60° and 120°. The reaction time, depending on the conditions used, is between a few minutes and several days. The boronic acid derivatives can be pre-pared by conventional methods or are commercially available. The reactions can be carried out analogously to the methods indicated in Suzuki et al., J. Am. Chem. Soc. 1989, 111, 314 ff. and in Suzuki et al. Chem. Rev. 1995, 95, 2457 ff.

Compounds of the formula III in which X is NH (formula III-1) are prepared, for example, in accordance with the following reaction scheme 2, where $SG_2$ is a hydroxyl-protecting group, as described above. The radicals Y, $R^5$ and $R^{5'}$ and the variables m and n in the formulae 4 to 6 are as defined in Claim 1. Ar in the compounds of the formula 5 has one of the meanings indicated above; Ar in compounds of the formula 5 is particularly preferably 4-nitrophenyl.

Reaction scheme 2:

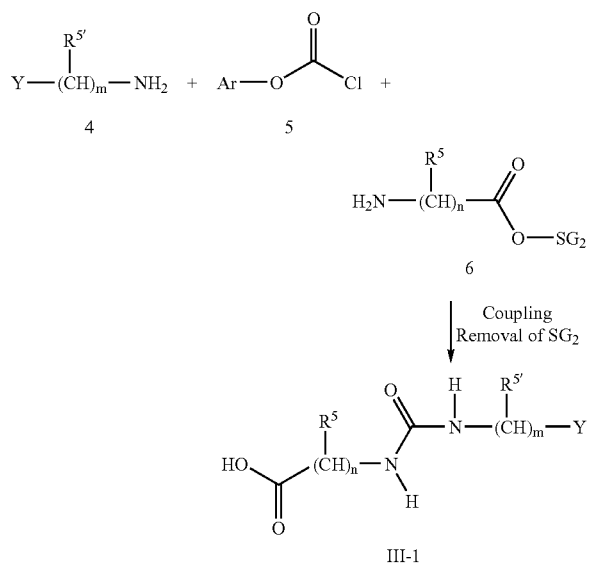

In a one-pot reaction, compounds of the formula 4 or salts thereof are reacted with a chloroformate of the formula 5, where Ar is preferably 4-nitrophenyl, and then reacted with an amine of the formula 6. Suitable auxiliary bases in the said reactions are known to the person skilled in the art. DIPEA (diisopropylethylamine) is preferably employed. Removal of the protecting group $SG_2$ under known conditions liberates the acid of the formula III-1.

Compounds of the formula III in which X is O (formula III-2) are prepared, for example, in accordance with the following reaction scheme 3, where $SG_2$ is a hydroxyl-protecting group, as described above. The radicals Y, $R^5$ and $R^{5'}$ and the variables m and n in the formulae 5 to 7 are as defined in Claim 1. Ar in the compounds of the formula 5 has one of the meanings indicated above; Ar in compounds of the formula 5 is particularly preferably 4-nitrophenyl.

Reaction scheme 3:

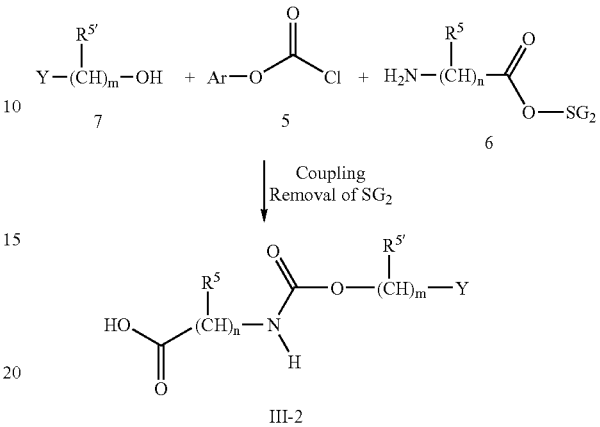

In a one-pot reaction, compounds of the formula 7 or salts thereof are reacted with a chloroformate of the formula 5, where Ar is preferably 4-nitrophenyl, and then reacted with an amine of the formula 6. Suitable auxiliary bases are known to the person skilled in the art. DIPEA (diisopropylethylamine) is preferably employed. Removal of the protecting group $SG_2$ under known conditions liberates the acid of the formula III-2.

The invention likewise relates to compounds of the formula III in which X, Y, $R^5$, $R^{5'}$, n and m are as defined in Claim 14.

Compounds of the formula III are important intermediates in the synthesis of the compounds of the formula I.

Compounds of the formula I are obtained by peptide-analogous coupling of the compounds of the formula II with a compound of the formula III or by peptide-analogous coupling of the compounds of the formula IV with a compound of the formula V under standard conditions.

Compounds of the formula IV are obtained by peptide-analogous coupling of a compound of the formula II with a carboxyl compound HOOC—[CH($R^5$)]$_n$—NHSG$_1$ under standard conditions, where $SG_1$ is an amino-protecting group as described above which is cleaved off after the coupling. Conventional methods of peptide synthesis are described, for example, in Houben-Weyl, l.c., Volume 15/II, 1974, pages 1 to 806.

The coupling reaction preferably succeeds in the presence of a dehydrating agent, for example a carbodiimide, such as dicyclohexylcarbodiimide (DCC), N-(3-dimethylaminopropyl)-N'-ethylcarbodiimide hydrochloride (EDC) or diisopropylcarbodiimide (DIC), furthermore, for example, propanephosphonic anhydride (cf. Angew. Chem. 1980, 92, 129), diphenylphosphoryl azide or 2-ethoxy-N-ethoxycarbonyl-1, 2-dihydroquinoline, in an inert solvent, for example a halogenated hydrocarbon, such as dichloromethane, an ether, such as tetrahydrofuran or dioxane, an amide, such as DMF or dimethylacetamide, a nitrile, such as acetonitrile, in dimethyl sulfoxide or in the presence of this solvent, at temperatures between about −10 and 40°, preferably between 0 and 30°. The reaction time, depending on the conditions used, is between a few minutes and several days.

It has proven particularly advantageous to add the coupling reagent TBTU (O-(benzotriazol-1-yl)-N,N,N',N'-tetramethyluronium tetrafluoroborate) or O-(benzotriazol-1-yl)-N,N,N',N'-tetramethyluronium hexafluorophosphate, since in the presence of one of these compounds only slight racemisation occurs and no cytotoxic by-products are formed.

Instead of compounds of the formula III, it is also possible to employ derivatives of compounds of the formula III, preferably a pre-activated carboxylic acid, or a carboxylic acid halide, a symmetrical or mixed anhydride or an active ester. Radicals of this type for activation of the carboxyl group in typical acylation reactions have been described in the literature (for example in the standard works, such as Houben-Weyl, Methoden der organischen Chemie [Methods of Organic Chemistry], Georg-Thieme-Verlag, Stuttgart). Activated esters are advantageously formed in situ, for example by addition of HOBt (1-hydroxybenzotriazole) or N-hydroxy-succinimide.

The reaction is generally carried out in an inert solvent; if a carboxylic acid halide is used, it is carried out in the presence of an acid-binding agent, preferably an organic base, such as triethylamine, dimethylaniline, pyridine or quinoline.

The addition of an alkali or alkaline-earth metal hydroxide, carbonate or bicarbonate or another salt of a weak acid of the alkali or alkaline-earth metals, preferably of potassium, sodium, calcium or caesium, may also be favourable.

Compounds of the formula I can alternatively be prepared by coupling of a compound of the formula 8

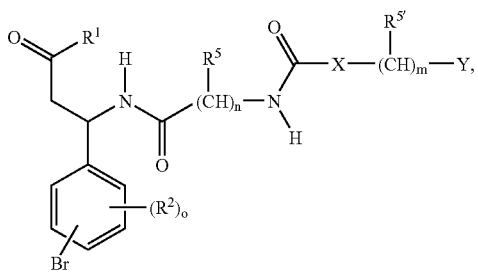

8 in which $R^1$, $R^2$, $R^5$, $R^{5'}$, X, Y, n, o and m are as defined in Claim 1, with an ($R^3$)-substituted phenylboronic acid under Suzuki conditions as described above. Hydroxyl or amino groups which are in protected form during the Suzuki coupling can be removed after the coupling under the conditions known in each case, as described above.

Compounds of the formula 8 are prepared analogously to compounds of the formula I, but with the corresponding starting material of the formula II or of the formula IV carrying a bromine substituent instead of the ($R^3$)$_p$-substituted phenyl ring:

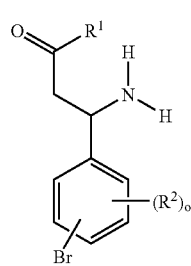

Starting material 8-II

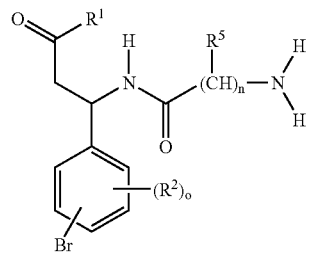

Starting material 8-IV

A base of the formula I can be converted into the associated acid-addition salt using an acid, for example by reaction of equivalent amounts of the base and the acid in an inert solvent, such as ethanol, followed by evaporation. Suitable acids for this reaction are, in particular, those which give physiologically acceptable salts. Thus, it is possible to use inorganic acids, for example sulfuric acid, sulfurous acid, dithionic acid, nitric acid, hydrohalic acids, such as hydrochloric acid or hydrobromic acid, phosphoric acids, such as, for example, orthophosphoric acid, sulfamic acid, furthermore organic acids, in particular aliphatic, alicyclic, araliphatic, aromatic or heterocyclic monobasic or polybasic carboxylic, sulfonic or sulfuric acids, for example formic acid, acetic acid, propionic acid, hexanoic acid, octanoic acid, decanoic acid, hexadecanoic acid, octadecanoic acid, pivalic acid, diethylacetic acid, malonic acid, succinic acid, pimelic acid, fumaric acid, maleic acid, lactic acid, tartaric acid, malic acid, citric acid, gluconic acid. ascorbic acid, nicotinic acid, isonicotinic acid, methane- or ethanesulfonic acid, benzenesulfonic acid, trimethoxybenzoic acid, adamantanecarboxylic acid, p-toluenesulfonic acid, glycolic acid, embonic acid, chlorophenoxyacetic acid, aspartic acid, glutamic acid, proline, glyoxylic acid, palmitic acid, para-chlorophenoxyisobutyric acid, cyclohexanecarboxylic acid, glucose 1-phosphate, naphthalenemono- and -disulfonic acids or lauryl-sulfuric acid. Salts with physiologically unacceptable acids, for example picrates, can be used to isolate and/or purify the compounds of the formula I.

On the other hand, compounds of the formula I can be converted into the corresponding metal salts, in particular alkali metal salts or alkaline earth metal salts, or into the corresponding ammonium salts, using bases (for example sodium hydroxide, potassium hydroxide, sodium carbonate or potassium carbonate).

The invention also relates to the compounds of the formula I according to Claim 1 and their physiologically acceptable salts or solvates as medicament active ingredients.

The invention furthermore relates to compounds of the formula I according to Claim 1 and their physiologically acceptable salts or solvates as integrin inhibitors.

The invention also relates to the compounds of the formula I according to Claim 1 and their physiologically acceptable salts or solvates for use in combating illnesses.

The invention furthermore relates to pharmaceutical preparations comprising at least one compound of the formula I and/or a physiologically acceptable salt or solvate thereof prepared, in particular, by non-chemical methods. The compounds of the formula I can be brought into a suitable dosage form here together with at least one solid, liquid and/or semiliquid excipient or assistant and, if desired, in combination with one or more further active ingredients.

These preparations can be used as medicaments in human or veterinary medicine. Suitable excipients are organic or inorganic substances which are suitable for enteral (for example oral), parenteral or topical administration and do not react with the novel compounds, for example water, vegetable oils, benzyl alcohols, alkylene glycols, polyethylene glycols, glycerol triacetate, gelatine, carbohydrates, such as lactose or starch, magnesium stearate, talc or vaseline. Suitable for oral administration are, in particular tablets, pills, coated tablets, capsules, powders, granules, syrups, juices or drops, suitable for rectal administration are suppositories, suitable for parenteral administration are solutions, preferably oily or aqueous solutions, furthermore suspensions, emulsions or implants, and suitable for topical application are ointments, creams or powders. The novel compounds can also be lyophilised and the resultant lyophilisates used, for example, for the preparation of injection preparations. The preparations indicated may be sterilised and/or comprise assistants, such as lubricants, preservatives. stabilisers and/or wetting agents, emulsifiers, salts for modifying the osmotic pressure, buffer substances, dyes, flavours and/or a plurality of further active ingredients, for example one or more vitamins. For administration as an inhalation spray, it is possible to use sprays in which the active ingredient is either dissolved or suspended in a propellant gas or propellant gas mixture (for example $CO_2$ or chlorofluorocarbons). The active ingredient is advantageously used here in micronised form, in which case one or more additional physiologically acceptable solvents may be present, for example ethanol. Inhalation solutions can be administered with the aid of conventional inhalers.

The compounds of the formula I and their physiologically acceptable salts or solvates can be used as integrin inhibitors in the combating of illnesses, in particular thromboses, cardiac infarction, coronary heart diseases, arteriosclerosis, tumours, osteoporosis, inflammations and infections.

The compounds of the formula I according to Claim 1 and/or their physiologically acceptable salts are also used in pathological processes which are maintained or propagated by angiogenesis, in particular in tumours, restenoses, diabetic retinopathy, or rheumatoid arthritis.

The substances according to the invention are generally administered analogously to other known commercially available peptides, but in particular analogously to the compounds described in WO 97/26250, preferably in doses of from about 0.05 to 500 mg, in particular from 0.5 to 100 mg, per dosage unit. The daily dose is preferably from about 0.01 to 2 mg/kg of body weight. However, the specific dose for each patient depends on a wide variety of factors, for example on the efficacy of the specific compound employed, on the age, body weight, general state of health, sex, on the diet, on the time and method of administration, on the rate of excretion, medicament combination and severity of the particular illness to which the therapy applies. Parenteral administration is preferred.

Furthermore, the compounds of the formula I can be used as integrin ligands for the production of columns for affinity chromatography for the purification of integrins.

In this method, the ligand, i.e. a compound of the formula I, is covalently coupled to a polymeric support via an anchor function, for example the carboxyl group.

Suitable polymeric support materials are the polymeric solid phases having preferably hydrophilic properties that are known in peptide chemistry, for example crosslinked polysugars, such as cellulose, sepharose or Sephadex$^R$, acrylamides, polyethylene glycol-based polymers or Tentakel$^R$ polymers.

The materials for affinity chromatography for integrin purification are prepared under conditions as are usual and known per se for the condensation of amino acids.

The compounds of the formula I have one or more centres of chirality and can therefore exist in racemic or optically active form. Racemates obtained can be resolved into the enantiomers mechanically or chemically by methods known per se. Diastereomers are preferably formed from the racemic mixture by reaction with an optically active resolving agent. Examples of suitable resolving agents are optically active acids, such as the D and L forms of tartaric acid, diacetyltartaric acid, dibenzoyltartaric acid, mandelic acid, malic acid, lactic acid, and the various optically active camphorsulfonic acids, such as β-camphorsulfonic acid. Resolution of the enantiomers with the aid of a column filled with an optically active resolving agent (for example dinitrobenzoylphenylglycine) is also advantageous; an example of a suitable eluent is a mixture of hexane/isopropanol/acetonitrile, for example in the volume ratio 82:15:3.

It is of course also possible to obtain optically active compounds of the formula I by the methods described above by using starting materials which are already optically active.

Above and below, all temperatures are given in ° C. In the following examples, "conventional work-up" means that, if necessary, water is added if necessary, depending on the constitution of the end product, the pH is adjusted to a value between 2 and 10, the mixture is extracted with ethyl acetate or dichloromethane, the phases are separated, the organic phase is dried over sodium sulfate and evaporated, and the product is purified by chromatography on silica gel, by preparative HPLC and/or by crystallisation. The purified compounds are, if desired, freeze-dried.

RT=retention time (in minutes) in the case of HPLC in the following systems:

column: Lichrosorb RP Select B 250×4.4 mm$^2$;
Chromolith SpeedROD, 50×4.6 mm$^2$.

The eluents used are gradients of acetonitrile (B) with 0.08% of TFA (trifluoroacetic acid) and water (A) with 0.1% of TFA. The gradient is indicated in per cent by volume of acetonitrile.

Preferred gradient: linear, t=0 min, A:B=80:20, t=15 min, A:B=0:100 (t=time) or linear, t=0 min, A:B=80:20, t=3–3.5 min, A:B=0:100.

Detection at 225 nm.

The compounds purified by preparative HPLC are generally isolated as trifluoroacetates. If an excess of NaOH is used during the cleaving-off from the support, the sodium salt of the corresponding compound or the zwitterion is obtained.

Mass spectrometry (MS).

EXAMPLE 1

Synthesis of 3-biphenyl-4-yl-3-{2-[3-(pyridin-2-ylamino)propoxycarbonylamino]ethanoylamino}propionic acid (1) 2.6 ml of diisopropylethylamine are added to a solution of 0.9 g of 3-(pyridin-2-ylamino)propan-1-ol in 3 ml of N,N-dimethylformamide. This solution is subsequently added dropwise to a solution of 1 g of 4-nitrophenyl chloroformate in 10 ml of dichloromethane. After the mixture has been stirred at room temperature for 1 hour, 0.7 g of tert-butyl aminoacetate and 0.8 ml of DIPEA are added, and the mixture is stirred for a further 2 hours. Conventional work-up gives tert-butyl [3-(pyridin-2-ylamino)propoxycarbonylamino]acetate, $R_f$=0.488 (ethyl acetate).

(2) 1 ml of trifluoroacetic acid is added to a solution of 0.6 g of tert-butyl [3-(pyridin-2-ylamino)propoxycarbonylamino]acetate in 10 ml of dichloromethane. After the mixture has been stirred at room temperature for 1 hour, the solvent is distilled off, and the product is co-distilled with toluene, giving the free acid [3-(pyridin-2-ylamino)propoxycarbonylamino]acetic acid.

(3) 4.1 g of diisopropylcarbodiimide (DIC) and 14.1 g of the solid phase polystyrene A OH (Rapp, Art. No. HA 1 400 00) are added to a solution of 14.1 g of 3-(4-bromophenyl)-3-(9H-fluoren-9-ylmethoxycarbonylamino)propionic acid in 100 ml of N,N-dimethylformamide, and 100 mg of dimethylaminopyridine (DMAP) are added. The reaction mixture is stirred at room temperature for 12 hours and then filtered. The resin is washed three times with 150 ml of each of DMF, dichloromethane and diethyl ether and dried. The resin-bound compound "AB" is obtained, where Pol denotes the solid phase polystyrene A OH without the functional OH group.

AB

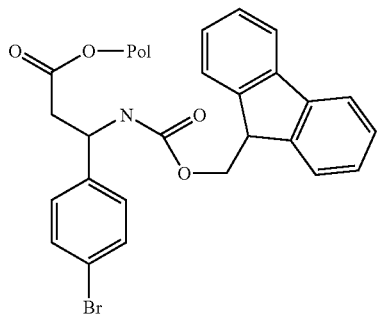

(4) 250 mg of tetrakis(triphenylphosphine)palladium(0) and 1.7 g of phenylboronic acid are added under an inert-gas atmosphere to a suspension of 5 g of the compound "AB" in 40 g of ethylene glycol dimethyl ether. The mixture is heated at the boiling point for 12 hours. After the reaction mixture has cooled, 100 ml of a 25% ammonium acetate solution are added, and the resin is filtered off. The resin is subsequently washed with 50 ml of each of the following solvents or acids: twice with dimethoxyethane (DME), once with water, once with 0.2 N hydrochloric acid, twice with DME, twice with dichloromethane and twice with methanol, giving resin-bound 3-biphenyl-4-yl-3-(9H-fluoren-9-ylmethoxycarbonylamino)propionic acid "BC".

BC

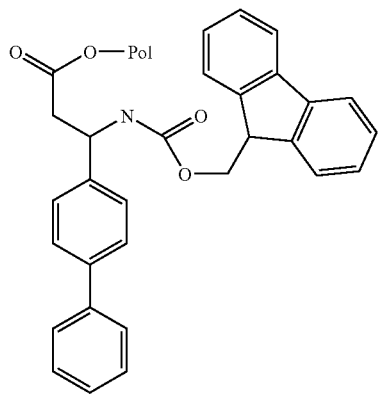

(5) 2 ml of piperidine are added to a suspension of 1 g of the solid phase "BC" in 2 ml of DMF, and the mixture is stirred for 30 minutes in order to remove the amino-protecting group. The resin is filtered off, washed with DMF and suspended in 10 ml of DMF. 0.3 g of [3-(pyridin-2-ylamino)propoxycarbonylamino]acetic acid, 0.4 g of TBTU and 0.4 ml of DIPEA are added to this suspension, and the mixture is stirred for 12 hours. The resin is filtered off and washed with DMF, dichloromethane and methanol.

For the cleaving off:
The resin (about 1 g) is stirred at room temperature for 5 hours in a mixture of 1 ml of 4N NaOH, 4 ml of MeOH and 10 ml of dioxane. The solid support is filtered off, and the cleavage solution is evaporated to dryness under reduced pressure.

Preparative HPLC give 3-biphenyl-4-yl-3-{2-[3-(pyridin-2-ylamino)propoxycarbonylamino]ethanoylamino}propionic acid trifluoroacetate, RT=7.41, MS (M+H)$^+$ 477.

EXAMPLE 2

Analogously to Example 1, the resin "BC" is reacted with [2-(pyridin-2-yl-amino)ethoxycarbonylamino]acetic acid (prepared analogously to Example 1 by reaction of 2-(pyridin-2-ylamino)ethanol with 4-nitrophenyl chloroformate and tert-butyl aminoacetate and cleavage of the ester). Cleavage from the support gives 3-biphenyl-4-yl-3-{2-[2-(pyridin-2-ylamino)ethoxycarbonylamino]ethanoylamino}propionic acid.

Preparative HPLC gives 3-biphenyl-4-yl-3-{2-[2-(pyridin-2-ylamino)ethoxycarbonylamino]ethanoylamino}propionic acid trifluoroacetate, RT=7.41 min, MS (M+H)$^+$ 463.

Methylation, i.e. stirring in methanolic hydrochloric acid (about 12 hours) followed by work-up, as described above, gives methyl 3-biphenyl-4-yl-3-{2-[2-(pyridin-2-ylamino)ethoxycarbonylamino]ethanoylamino}propionate, RT=8.64 min, MS (M+H)$^+$ 477.

EXAMPLE 3

The resin "BC" is reacted analogously to Example 1 with {3-[3-(pyridin-2-yl-amino)propyl]ureido}acetic acid (prepared analogously to Example 1 by reaction of N$^1$-pyridin-2-ylpropane-1,3-diamine dihydrochloride with 4-nitrophenyl chloroformate and tert-butyl aminoacetate and cleavage of the ester). Cleavage from the support gives 3-biphenyl-4-yl-3-(2-{3-[3-(pyridin-2-ylamino)propyl]ureido}ethanoylamino)propionic acid.

Preparative HPLC gives 3-biphenyl-4-yl-3-(2-{3-[3-(pyridin-2-ylamino)propyl]ureido}ethanoylamino)propionic acid trifluoroacetate, RT=7.71 min, MS (M+H)$^+$ 476.

Analogously to Example 1, the resin "BC" is reacted with {3-[4-(pyridin-2-yl-amino)butyl]ureido}acetic acid (prepared analogously to Example 1 by reaction of N$^1$-pyridin-2-ylbutane-1,4-diamine dihydrochloride with 4-nitrophenyl chloroformate and tert-butyl aminoacetate and cleavage of the ester). Cleavage from the support gives 3-biphenyl-4-yl-3-(2-{3-[4-(pyridin-2-ylamino)butyl]ureido}ethanoylamino)propionic acid.

Preparative HPLC gives 3-biphenyl-4-yl-3-(2-{3-[4-(pyridin-2-ylamino)butyl]ureido}ethanoylamino)propionic acid trifluoroacetate, RT=7.25 min, MS (M+H)$^+$ 490.

Analogously to Example 1, the resin "BC" is reacted with {3-[2-(pyridin-2-yl-amino)ethyl]ureido}acetic acid (prepared analogously to Example 1 by reaction of N$^1$-pyridin-2-ylethane-1,2-diamine dihydrochloride with 4-nitrophenyl chloroformate and tert-butyl aminoacetate and cleavage of the ester). Cleavage from the support gives 3-biphenyl-4-yl-3-(2-{3-[2-(pyridin-2-ylamino)ethyl]ureido}ethanoylamino)propionic acid.

Preparative HPLC gives 3-biphenyl-4-yl-3-(2-{3-[2-(pyridin-2-ylamino)ethyl]-ureido}ethanoylamino)propionic acid trifluoroacetate, RT=7.17 min, MS (M+H)$^+$ 462.

Analogously to Example 1, the resin "BC" is reacted with {3-[2-(1H-benzimidazol-2-ylamino)ethyl]ureido}acetic acid (prepared analogously to Example 1 by reaction of $N^1$-(1H-benzimidazol-2-yl)ethane-1,2-diamine dihydrochloride with 4-nitrophenyl chloroformate and tert-butyl aminoacetate and cleavage of the ester). Cleavage from the support gives 3-(2-{3-[2-(1H-benzimidazol-2-ylamino)ethyl]ureido}ethanoylamino)-3-biphenyl-4-ylpropionic acid.

Preparative HPLC gives 3-(2-{3-[2-(1H-benzimidazol-2-ylamino)ethyl]-ureido}ethanoylamino)-3-biphenyl-4-ylpropionic acid trifluoroacetate, RT=7.09 min, MS (M+H)$^+$ 501.

Analogously to Example 1, the resin "BC" is reacted with {3-[3-(1H-benzimidazol-2-ylamino)propyl]ureido}acetic acid (prepared analogously to Example 1 by reaction of $N^1$-(1H-benzimidazol-2-yl)propane-1,3-diamine dihydrochloride with 4-nitrophenyl chloroformate and tert-butyl aminoacetate and cleavage of the ester). Cleavage from the support gives 3-(2-{3-[3-(1H-benzimidazol-2-ylamino)propyl]ureido}ethanoylamino)-3-biphenyl-4-ylpropionic acid.

Preparative HPLC gives 3-(2-{3-[3-(1H-benzimidazol-2-ylamino)propyl]-ureido}ethanoylamino)-3-biphenyl-4-ylpropionic acid trifluoroacetate. RT=8.05 min, MS (M+H)$^+$ 515.

EXAMPLE 4

Analogously to Example 4, the resin "CD"

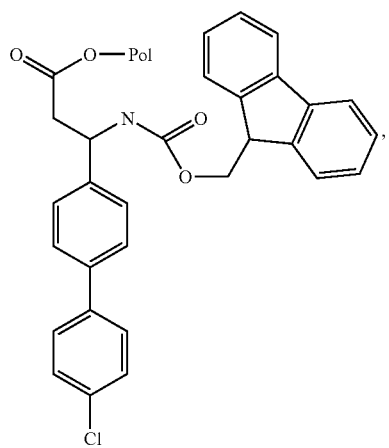

CD prepared by reaction of the resin AB with 4-chlorophenylboronic acid as described in Example 1, is reacted with {3-[3-(pyridin-2-ylamino)propyl]ureido}acetic acid (prepared analogously to Example 1 by reaction of $N^1$-pyridin-2-ylpropane-1,3-diamine dihydrochloride with 4-nitrophenyl chloroformate and tert-butyl aminoacetate and cleavage of the ester) and cleaved off from the support, giving 3-(4'-chlorobiphenyl-4-yl)-3-(2-{3-[3-(pyridin-2-ylamino)propyl]ureido}ethanoylamino)propionic acid.

Preparative HPLC gives 3-(4'-chlorobiphenyl-4-yl)-3-(2-{3-[3-(pyridin-2-yl-amino)propyl]ureido}ethanoylamino) propionic acid trifluoroacetate, RT=7.92 min, MS (M+H)$^+$ 510.

EXAMPLE 5

1. Analogously to Example 1-3, the resin "DE"

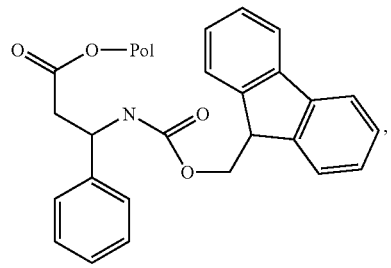

DE prepared by reaction of 3-(phenyl)-3-(9H-fluoren-9-ylmethoxycarbonylamino)propionic acid with the solid phase polystyrene A OH (Rapp, Art. No. HA 1 400 00), is reacted with {3-[3-(pyridin-2-ylamino)propyl]ureido}acetic acid (prepared analogously to Example 1 by reaction of $N^1$-pyridin-2-ylpropane-1,3-diamine dihydrochloride with 4-nitrophenyl chloroformate and tert-butyl aminoacetate and cleavage of the ester) and cleaved off from the support, giving 3-phenyl-3-(2-{3-[3-(pyridin-2-ylamino)propyl]ureido}ethanoylamino)propionic acid.

Preparative HPLC gives 3-phenyl-3-(2-{3-[3-(pyridin-2-ylamino)propyl]-ureido}ethanoylamino)propionic acid trifluoroacetate, RT=4.99 min, MS (M+H)$^+$ 400.

2. Analogously to Example 1-3, the resin "DE" is reacted with [3-(pyridin-2-ylamino)propoxycarbonylamino]acetic acid (prepared in Example 1) and cleaved off from the support, giving 3-phenyl-3-{2-[3-(pyridin-2-ylamino)propoxycarbonylamino]ethanoylamino}propionic acid.

Preparative HPLC gives 3-phenyl-3-{2-[3-(pyridin-2-ylamino)propoxycarbonylamino]ethanoylamino}propionic acid trifluoroacetate, RT=5.28 min, MS (M+H)$^+$ 401.

EXAMPLE 6

Analogously to Example 1, the resin "BC" is reacted with [1-methyl-2-(pyridin-2-ylamino)ethoxycarbonylamino]acetic acid (prepared analogously to Example 1 by reaction of 1-methyl-2-(pyridin-2-ylamino)ethanol with 4-nitrophenyl chloroformate and tert-butyl aminoacetate and cleavage of the ester). Cleavage from the support gives 3-biphenyl-4-yl-3-{2-[1-methyl-2-(pyridin-2-ylamino)ethoxycarbonylamino]ethanoylamino}propionic acid.

Preparative HPLC gives 3-biphenyl-4-yl-3-{2-[1-methyl-2-(pyridin-2-ylamino)ethoxycarbonylamino]ethanoylamino}propionic acid trifluoroacetate, RT=3.07 min, MS (M+H)$^+$ 477.

Analogously to Example 1, the resin "BC" is reacted with [2-(pyridin-2-ylamino)propoxycarbonylamino]acetic acid (prepared analogously to Example 1 by reaction of 2-(pyridin-2-ylamino)propan-1-ol with 4-nitrophenyl chloroformate and tert-butyl aminoacetate and cleavage of the ester). Cleavage from the support gives 3-biphenyl-4-yl-3-{2-[2-(pyridin-2-ylamino)propoxycarbonylamino]ethanoylamino}propionic acid.

Preparative HPLC gives 3-biphenyl-4-yl-3-{2-[2-(pyridin-2-ylamino)propoxycarbonylamino]ethanoylamino}propionic acid trifluoroacetate, RT=3.25 min, MS (M+H)$^+$ 517.

Analogously to Example 1, the resin "BC" is reacted with [2-(1H-benzimidazol-2-ylamino)ethoxycarbonylamino]acetic acid (prepared analogously to Example 1 by reaction of 2-(1H-benzimidazol-2-ylamino)ethanol with 4-nitrophenyl chloroformate and tert-butyl aminoacetate and cleavage of the ester). Cleavage from the support gives 3-{2-[2-(1H-benzimidazol-2-ylamino)ethoxycarbonylamino]ethanoylamino}-3-biphenyl-4-ylpropionic acid.

Preparative HPLC gives 3-{2-[2-(1H-benzimidazol-2-ylamino)ethoxycarbonylamino]ethanoylamino}-3-biphenyl-4-ylpropionic acid trifluoroacetate, RT=3.20 min, MS (M+H)+ 502.

EXAMPLE 7

Analogously to Example 1, the resin "CD" is reacted with [2-(pyridin-2-ylamino)ethoxycarbonylamino]acetic acid (prepared analogously to Example 1 by reaction of 2-(pyridin-2-ylamino)ethanol with 4-nitrophenyl chloroformate and tert-butyl aminoacetate and cleavage of the ester). Cleavage from the support gives 3-(4'-chlorobiphenyl-4-yl)-3-{2-[2-(pyridin-2-ylamino)ethoxycarbonylamino]ethanoylamino}propionic acid.

Preparative HPLC gives 3-(4'-chlorobiphenyl-4-yl)-3-{2-[2-(pyridin-2-ylamino)ethoxycarbonylamino]ethanoylamino}propionic acid trifluoroacetate, RT=8.00 min, MS (M+H)+ 497.

EXAMPLE 8

Analogously to Example 1-3, the resin "EF"

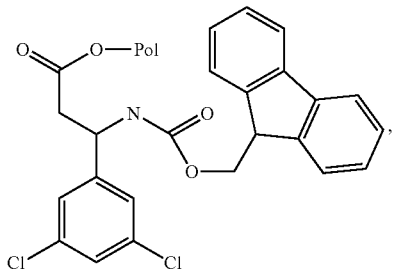

EF prepared by reaction of 3-(3,5-dichlorophenyl)-3-(9H-fluoren-9-ylmethoxycarbonylamino)propionic acid with the solid phase polystyrene A OH (Rapp, Art. No. HA 1 400 00), is reacted with [2-(pyridin-2-ylamino)ethoxycarbonylamino]acetic acid and cleaved off from the support, giving 3-(3,5-dichlorophenyl)-3-{2-[2-(pyridin-2-ylamino)ethoxycarbonylamino]ethanoylamino}propionic acid.

Preparative HPLC gives 3-(3,5-dichlorophenyl)-3-{2-[2-(pyridin-2-ylamino)ethoxycarbonylamino]ethanoylamino}propionic acid trifluoroacetate, RT=2.75 min, MS (M+H)+ 456.

EXAMPLE 9

1. Analogously to Example 8, the resin "EF" is reacted with [2-(6-methylpyridin-2-ylamino)ethoxycarbonylamino]acetic acid (prepared analogously to Example 1 by reaction of 2-(6-methylpyridin-2-ylamino)ethanol with 4-nitrophenyl chloroformate and tert-butyl aminoacetate and cleavage of the ester). Cleavage from the support gives 3-(3,5-dichlorophenyl)-3-{2-[2-(6-methylpyridin-2-ylamino)ethoxycarbonylamino]ethanoylamino}propionic acid.

Preparative HPLC gives 3-(3,5-dichlorophenyl)-3-{2-[2-(6-methylpyridin-2-ylamino)ethoxycarbonylamino]ethanoylamino}propionic acid trifluoroacetate, RT=2.83 min, MS (M+H)+ 470.

2. Ethylation of 3-(3,5-dichlorophenyl)-3-{2-[2-(6-methylpyridin-2-yl-amino)ethoxycarbonylamino]ethanoylamino}propionic acid by stirring in ethanolic hydrochloric acid and subsequent work-up, as described above, gives ethyl 3-(3,5-dichlorophenyl)-3-{2-[2-(6-methylpyridin-2-ylamino)ethoxycarbonylamino]ethanoylamino}propionate, RT=3.31 min, MS (M+H)+ 498.

EXAMPLE 10

Analogously to Example 8, the resin "EF" is reacted with [3-(pyridin-2-ylamino)propoxycarbonylamino]acetic acid (prepared analogously to Example 1 by reaction of 3-(pyridin-2-ylamino)propanol with 4-nitrophenyl chloroformate and tert-butyl aminoacetate and cleavage of the ester). Cleavage from the support gives 3-(3,5-dichlorophenyl)-3-{2-[3-(pyridin-2-ylamino)propoxycarbonylamino]ethanoylamino}propionic acid.

Preparative HPLC gives 3-(3,5-dichlorophenyl)-3-{2-[3-(pyridin-2-ylamino)propoxycarbonylamino]ethanoylamino}propionic acid trifluoroacetate, RT=2.77 min, MS (M+H)+ 470.

EXAMPLE 11

Analogously to Example 1-3, the resin "FG"

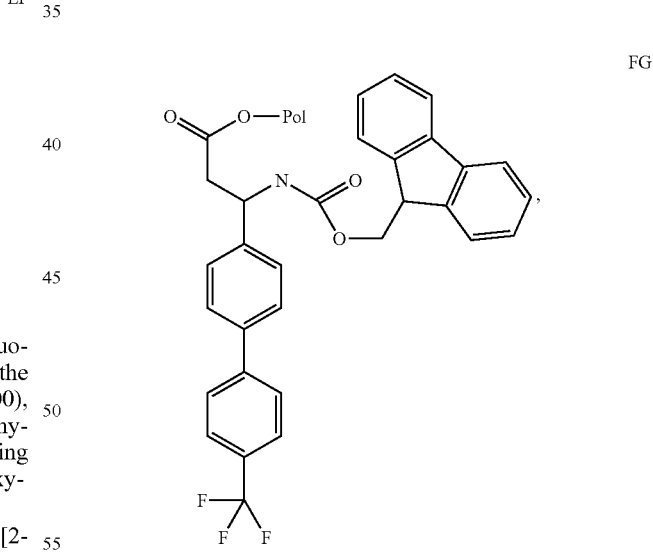

FG prepared by reaction of the resin AB with 4-(trifluoromethyl)phenylboronic acid according to Example 1, is reacted with [2-(pyridin-2-ylamino)ethoxycarbonylamino]acetic acid and cleaved off from the support, giving 3-{2-[2-(pyridin-2-ylamino)ethoxycarbonylamino]ethanoylamino}-3-(4'-trifluoromethylbiphenyl-4-yl)propionic acid.

Preparative HPLC gives 3-{2-[2-(pyridin-2-ylamino)ethoxycarbonylamino]ethanoylamino}-3-(4'-trifluoromethylbiphenyl-4-yl)propionic acid trifluoroacetate, RT=8.27 min, MS (M+H)+ 531.

EXAMPLE 12

Analogously to Example 1-3, the resin "GH"

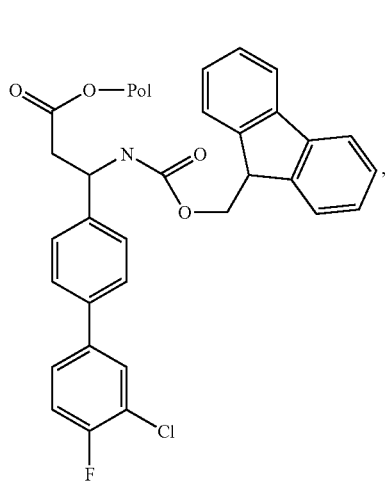

GH prepared by reaction of the resin AB with 3-chloro-4-fluorophenylboronic acid according to Example 1, is reacted with [2-(pyridin-2-ylamino)ethoxycarbonylamino]acetic acid and cleaved off from the support, giving 3-(3'-chloro-4'-fluorobiphenyl-4-yl)-3-{2-[2-(pyridin-2-ylamino)ethoxycarbonylamino]ethanoylamino}propionic acid.

Preparative HPLC gives 3-(3'-chloro-4'-fluorobiphenyl-4-yl)-3-{2-[2-(pyridin-2-ylamino)ethoxycarbonylamino]ethanoylamino}propionic acid trifluoroacetate, RT=7.87 min, MS (M+H)+ 515.

EXAMPLE 13

Analogously to Example 1-3, the resin "HI"

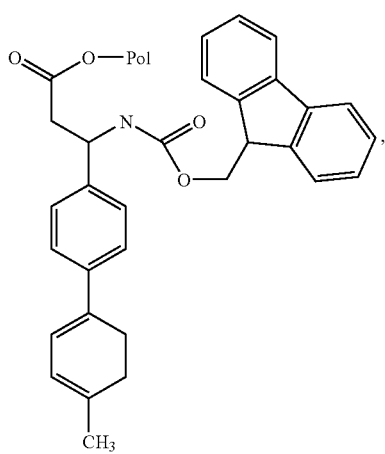

HI prepared by reaction of the resin AB with 4-methylphenylboronic acid according to Example 1, is reacted with [2-(pyridin-2-ylamino)ethoxycarbonylamino]acetic acid and cleaved off from the support, giving 3-(4'-methylbiphenyl-4-yl)-3-{2-[2-(pyridin-2-ylamino)ethoxycarbonylamino]ethanoylamino}propionic acid.

Preparative HPLC gives 3-(4'-methylbiphenyl-4-yl)-3-{2-[2-(pyridin-2-ylamino)ethoxycarbonylamino]ethanoylamino}propionic acid trifluoroacetate, RT=7.25 min, MS (M+H)+ 477.

EXAMPLE 14

Analogously to Example 1-3, the resin "IJ"

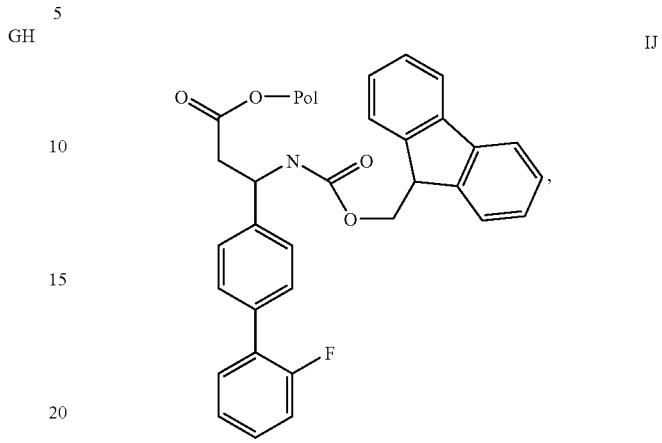

IJ prepared by reaction of the resin AB with 2-fluorophenylboronic acid according to Example 1, is reacted with [2-(pyridin-2-ylamino)ethoxycarbonylamino]acetic acid and cleaved off from the support, giving 3-(2'-fluorobiphenyl-4-yl)-3-{2-[2-(pyridin-2-ylamino)ethoxycarbonylamino]ethanoylamino}propionic acid.

Preparative HPLC gives 3-(2'-fluorobiphenyl-4-yl)-3-{2-[2-(pyridin-2-ylamino)ethoxycarbonylamino]ethanoylamino}propionic acid trifluoroacetate, RT=7.47 min, MS (M+H)+ 481.

EXAMPLE 15

Analogously to Example 1-3, the resin "JK"

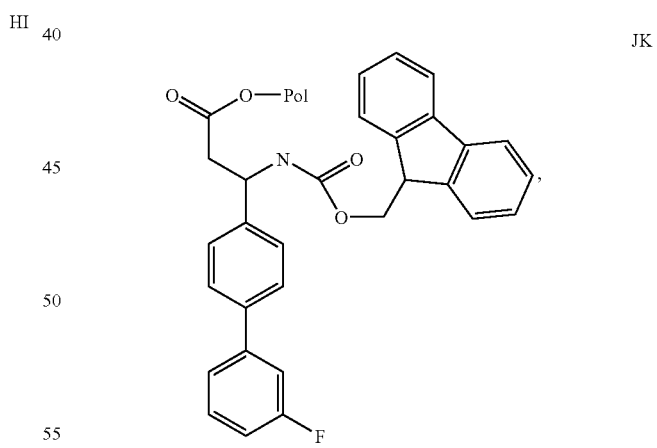

JK prepared by reaction of the resin AB with 3-fluorophenylboronic acid according to Example 1, is reacted with [2-(pyridin-2-ylamino)ethoxycarbonylamino]acetic acid and cleaved off from the support, giving 3-(3'-fluorobiphenyl-4-yl)-3-{2-[2-(pyridin-2-ylamino)ethoxycarbonylamino]ethanoylamino}propionic acid.

Preparative HPLC gives 3-(3'-fluorobiphenyl-4-yl)-3-{2-[2-(pyridin-2-ylamino)ethoxycarbonylamino]ethanoylamino}propionic acid trifluoroacetate, RT=7.55 min, MS (M+H)+ 481.

EXAMPLE 16

Analogously to Example 1-3, the resin "KL"

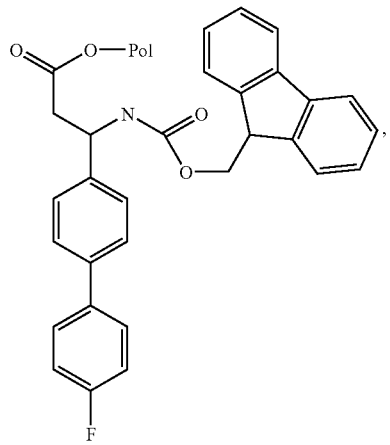

prepared by reaction of the resin AB with 4-fluorophenylboronic acid according to Example 1 is reacted with [2-(pyridin-2-ylamino)ethoxycarbonylamino]acetic acid and cleaved off from the support, giving 3-(4'-fluorobiphenyl-4-yl)-3-{2-[2-(pyridin-2-ylamino)ethoxycarbonylamino]ethanoylamino}propionic acid.

Preparative HPLC gives 3-(4'-fluorobiphenyl-4-yl)-3-{2-[2-(pyridin-2-ylamino)ethoxycarbonylamino]ethanoylamino}propionic acid trifluoroacetate, RT=7.71 min, MS (M+H)$^+$ 481.

Subsequent ethylation analogously to Example 9.2 gives ethyl 3-(4'-fluorobiphenyl-4-yl)-3-{2-[2-(pyridin-2-ylamino)ethoxycarbonylamino]ethanoylamino}propionate, RT=8.99, MS (M+H)$^+$ 509.

EXAMPLE 17

Analogously to Example 1-3, the resin "LM"

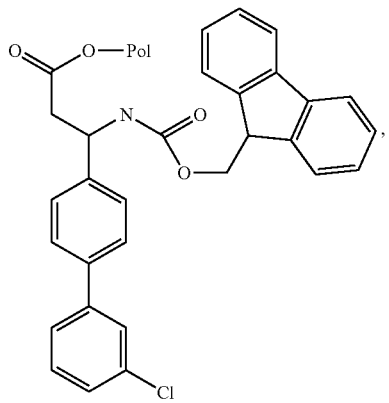

prepared by reaction of the resin AB with 3-chlorophenylboronic acid according to Example 1, is reacted with [2-(pyridin-2-ylamino)ethoxycarbonylamino]acetic acid and cleaved off from the support, giving 3-(3'-chlorobiphenyl-4-yl)-3-{2-[2-(pyridin-2-ylamino)ethoxycarbonylamino]ethanoylamino}propionic acid.

Preparative HPLC gives 3-(3'-chlorobiphenyl-4-yl)-3-{2-[2-(pyridin-2-ylamino)ethoxycarbonylamino]ethanoylamino}propionic acid trifluoroacetate. RT=8.00 min, MS (M+H)$^+$ 497.

EXAMPLE 18

Resolution of the racemate 3-biphenyl-4-yl-3-{2-[2-(pyridin-2-ylamino)ethoxycarbonylamino]ethanoylamino}propionic acid, prepared in accordance with Example 2, is carried out on a chiral HPLC phase (Hibow 25×5 cm column packed with Chiralpak AD (20 μm) from Chiral Technologies Inc. (Order No. 19020)). Eluent: acetonitrile (100%), flow rate: 60 ml/min, pressure: 30 bar.

(3S)-3-Biphenyl-4-yl-3-{2-[2-(pyridin-2-ylamino)ethoxycarbonylamino]ethanoylamino}propionic acid, RT=7.28 min, MS (M+H)$^+$ 463; and (3R)-3-biphenyl-4-yl-3-{2-[2-(pyridin-2-ylamino)ethoxycarbonylamino]ethanoylamino}propionic acid, RT=7.33 min, MS (M+H)$^+$ 463 are obtained.

Methylation under the conditions of Example 2 gives methyl (3S)-3-biphenyl-4-yl-3-{2-[2-(pyridin-2-ylamino)ethoxycarbonylamino]ethanoylamino}propionate and methyl (3R)-3-biphenyl-4-yl-3-{2-[2-(pyridin-2-ylamino)ethoxycarbonylamino]ethanoylamino}propionate.

The examples below relate to pharmaceutical preparations:

EXAMPLE A

Injection Vials

A solution of 100 g of an active ingredient of the formula I and 5 g of disodium hydrogenphosphate in 3 l of bidistilled water is adjusted to pH 6.5 using 2N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient of the formula I is melted with 100 g of soya lecithin and 1400 g of cocoa butter, poured into moulds and allowed to cool. Each suppository contains 20 mg of active ingredient.

EXAMPLE C

Solution

A solution is prepared from 1 g of an active ingredient of the formula I, 9.38 g of NaH$_2$PO$_4$.2 H$_2$O, 28.48 g of Na$_2$HPO$_4$.12 H$_2$O and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient of the formula I are mixed with 99.5 g of Vaseline under aseptic conditions.

EXAMPLE E

Tablets

A mixture of 1 kg of active ingredient of the formula I, 4 kg of lactose, 1.2 kg of potato starch, 0.2.kg of talc and 0.1 kg of magnesium stearate is pressed to give tablets in a conventional manner in such a way that each tablet contains 10 mg of active ingredient.

EXAMPLE F

Coated Tablets

Tablets are pressed analogously to Example E and subsequently coated in a conventional manner with a coating of sucrose, potato starch, talc, tragacanth and dye.

EXAMPLE G

Capsules 2 kg of active ingredient of the formula I are introduced into hard gelatine capsules in a conventional manner in such a way that each capsule contains 20 mg of the active ingredient.

EXAMPLE H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

EXAMPLE I

Inhalation Spray 14 g of active ingredient of the formula I are dissolved in 10 l of isotonic NaCl solution, and the solution is transferred into commercially available spray containers with a pump mechanism. The solution can be sprayed into the mouth or nose. One spray shot (about 0.1 ml) corresponds to a dose of about 0.14 mg.

The invention claimed is:

1. A compound of the formula I

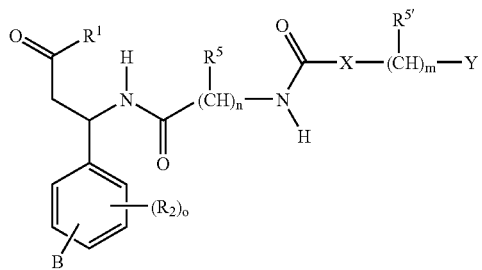

wherein

| | |
|---|---|
| X | is O or $NR^5$, |
| Y | is —$N(R^5)R^4$, —$C(=NR^7)$—$NHR^7$ or —$C(=NR^9)$—$NHR^7$, |
| B | is H or ![phenyl with $(R^3)_p$] |
| R | is H, A, cycloalkyl, Ar, arylalkyl or Pol, |
| $R^1$ | is OR or $N(R)_2$, |
| $R^2$ and $R^3$ | each is, independently of one another, H, A, Hal, $NO_2$, OR, $N(R)_2$, CN, CO—R, $SO_3R$, $SO_2R$, NH—C(O)A or SR, |
| $R^4$ | is H, $R^7$, —C(=$NR^7$)—$NHR^7$, —C(=$NR^9$)—$NHR^7$, —C(=CH—$NO_2$)—$NHR^7$ or Het, |
| $R^5$ and $R^{5'}$ | each is, independently of one another, H or A, |
| $R^6$ | is Hal or $NO_2$, |
| $R^7$ | is H, —C(O)$R^8$, —C(O)—Ar, $R^8$, COO$R^8$, COO—$(CH_2)_o$—Ar, $SO_2$—Ar, $SO_2R^8$ or $SO_2$-Het, |
| $R^8$ | is A or cycloalkyl, |
| $R^9$ | is CN or $NO_2$, |
| A | is alkyl having from 1 to 8 carbon atoms, where the alkyl groups may be monosubstituted or polysubstituted by $R^6$ and/or their alkyl carbon chain may be interrupted by —O—, |
| Ar | is phenyl, naphthyl, anthryl or biphenylyl, each of which is unsubstituted or monosubstituted, disubstituted or trisubstituted by A, OH, OA, CN, $NO_2$ or Hal, |
| cycloalkyl | is cycloalkyl having from 3 to 15 carbon atoms, |
| Hal | is F, Cl, Br or I, |
| Het | is a saturated, partially unsaturated or fully unsaturated monocyclic or bicyclic heterocyclic radical having from 5 to 10 ring members, where 1 or 2 N and/or 1 or 2 S or O atoms may be present, and the heterocyclic radical may be monosubstituted or disubstituted by =O, A, $NO_2$, NHCOA or NHA, |
| Pol | is a solid phase with no terminal functional group, |
| n and m | each is, independently of one another, 1, 2, 3, 4, 5 or 6, |
| o | is 1, 2, 3 or 4, and |
| p | is 1, 2, 3, 4 or 5, |

2. A compound of the formula I according to claim 1, wherein $R^2$ is OR.

3. A compound of the formula I according to claim 1, wherein

| | |
|---|---|
| $R^1$ | is OR and |
| X | is O. |

4. A compound of the formula I according to claim 1, wherein

| | |
|---|---|
| $R^1$ | is OR and |
| X | is $NR^5$. |

5. A compound according to claim 1, which is:
 a) 3-biphenyl-4-yl-3-{2-[3-(pyridin-2-ylamino)propoxycarbonylamino]ethanoylamino}propionic acid,
 b) 3-biphenyl-4-yl-3-{2-[3-(pyridin-2-ylamino)ethoxycarbonylamino]ethanoylamino}propionic acid,
 c) 3-(3'-chlorobiphenyl-4-yl)-3-{2-[2-(pyridin-2-ylamino)ethoxycarbonylamino]ethanoylamino}propionic acid,
 d) 3-(4'-chlorobiphenyl-4-yl)-3-{2-[2-(pyridin-2-ylamino)ethoxycarbonylamino]ethanoylamino}propionic acid,
 e) 3-(3'-fluorobiphenyl-4-yl)-3-{2-[2-(pyridin-2-ylamino)ethoxycarbonylamino]ethanoylamino}propionic acid,
 f) 3-(2'-fluorobiphenyl-4-yl)-3-{2-[2-(pyridin-2-ylamino)ethoxycarbonylamino]ethanoylamino}propionic acid,
 g) 3-(4'-methylbiphenyl-4-yl)-3-{2-[2-(pyridin-2-ylamino)ethoxycarbonylamino]ethanoylamino}propionic acid, h) 3-(3'-chloro-4'-fluorobiphenyl-4-yl)-3-{2-[2-(pyridin-2-ylamino)ethoxycarbonylamino]ethanoylamino}propionic acid, i) 3-{2-[2-(pyridin-2-ylamino)ethoxycarbonylamino]ethanoylamino}-3-(4'-trifluoromethylbiphenyl-4-yl)propionic acid, j) 3-{2-[2-(1H-benzimidazol-2-ylamino)ethoxycarbonylamino]ethanoyl-amino}-3-biphenyl-4-ylpropionic acid, k) (3R)-3-biphenyl-4-yl-3-{2-[2-(pyridin-2-ylamino)ethoxycarbonylamino]ethanoylamino}propionic acid, l) methyl 3-biphenyl-4-yl-3-{2-[2-(pyridin-2-ylamino)ethoxycarbonylamino]ethanoylamino}propionate, m) 3-(3,5-dichlorophenyl)-3-{2-[2-(pyridin-2-ylamino)ethoxycarbonylamino]ethanoylamino}propionic acid, n) 3-biphenyl-4-yl-3-(2-{3-[3-(pyridin-2-ylamino)propyl]ureido}ethanoyl-amino)propionic acid, o) 3-(2-{3-[2-(1H-benzimidazol-2-ylamino)ethyl]ureido}ethanoylamino)-3-biphenyl-4-ylpropionic acid, p) 3-biphenyl-4-yl-3-(2-{3-[2-(pyridin-2-ylamino)ethyl]ureido}ethanoyl-amino)propionic acid, q) 3-(4'-chlorobiphenyl-4-yl)-3-(2-{3-[3-(pyridin-2-ylamino)propyl]ureido}ethanoylamino)propionic acid, r) 3-(2-{3-[3-(1H-benzimidazol-2-ylamino)propyl]ureido}ethanoyl-amino)-3-biphenyl-4-ylpropionic acid, or a physiologically acceptable salt or solvate thereof.

6. A process for preparing a compound of the formula I according to claim 1, or a physiologically acceptable salt or solvate thereof, comprising:

(a) reacting a compound of the formula II

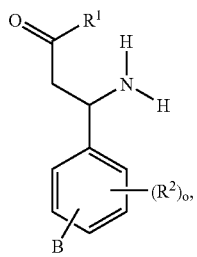

with the proviso that R≠H, and the free hydroxyl or amino groups as substituents R² or R³ are protected by a protecting group, with a compound of the formula III

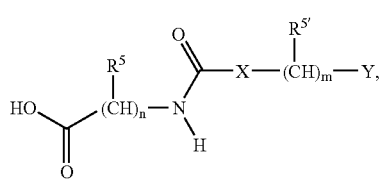

and, optionally converting the radical R≠H into the radical R═H, and removing any protecting groups on R₂ and/or R³, or (b) reacting a compound of the formula IV

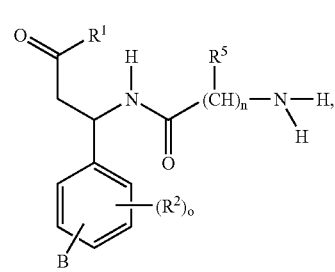

with the proviso that R≠H, and the free hydroxyl or amino groups as substituents R² or R³ are protected by a protecting groups, with a compound of the formula V

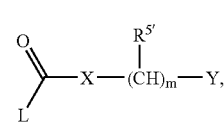

wherein L is Cl, Br, OH or a reactive, esterified OH group, and optionally converting, the radical R≠H into the radical R═H, and removing any protecting groups on R² and/or R³, or (c) in a compound of the formula I, converting one or more radicals R, R¹, R², R³, R⁴ and/or R⁵ into one or more radicals R, R¹, R², R³, R⁴ and/or R⁵ by, vii) alkylating a hydroxyl group, viii) hydrolysing an ester group to a carboxyl group, ix) esterifying a carboxyl group, x) alkylating an amino group, xi) reacting an aryl bromide or iodide with boronic acids by a Suzuki coupling to give the corresponding coupling products, or xii) acylating an amino group, and/or converting a basic or acidic compound of the formula I into its salt or solvate by treatment with an acid or base wherein

| | |
|---|---|
| X | is O or NR⁵, |
| Y | is —N(R⁵)R⁴, —C(═NR⁷)—NHR⁷ or —C(═NR⁹)—NHR⁷, |
| B | is H or 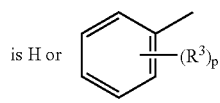 |
| R | is H, A, cycloalkyl, Ar, arylalkyl or Pol, |
| R¹ | is OR or N(R)₂, |
| R² and R³ | each is, independently of one another, H, A, Hal, NO₂, OR, N(R)₂, CN, CO—R, SO₃R, SO₂R, NH—C(O)A or SR, |
| R⁴ | is H, R⁷, —C(═NR⁷)—NHR⁷, —C(═NR⁹)—NHR⁷, —C(═CH—NO₂)—NHR⁷ or Het, |
| R⁵ and R⁵' | each is, independently of one another, H or A, |
| R⁶ | is Hal or NO₂, |
| R⁷ | is H, —C(O)R⁸, —C(O)—Ar, R⁸, COOR⁸, COO—(CH₂)ₒ—Ar, SO₂—Ar, SO₂R⁸ or SO₂-Het, |
| R⁸ | is A or cycloalkyl, |

| | |
|---|---|
| R⁹ | is CN or NO₂, |
| A | is alkyl having from 1 to 8 carbon atoms, where the alkyl groups may be monosubstituted or polysubstituted by R⁶ and/or their alkyl carbon chain may be interrupted by —O—, |
| Ar | is phenyl, naphthyl, anthryl or biphenylyl, each of which is unsubstituted or monosubstituted, disubstituted or trisubstituted by A, OH, OA, CN, NO₂ or Hal, |
| cycloalkyl | is cycloalkyl having from 3 to 15 carbon atoms, |
| Hal | is F, Cl, Br or I, |
| Het | is a saturated, partially unsaturated or fully unsaturated monocyclic or bicyclic heterocyclic radical having from 5 to 10 ring members, where 1 or 2 N and/or 1 or 2 S or O atoms may be present, and the heterocyclic radical may be monosubstituted or disubstituted by =O, A, NO₂, NHCOA or NHA, |
| Pol | is a solid phase with no terminal functional group, |
| n and m | each is, independently of one another, 1, 2, 3, 4, 5 or 6, |
| o | is 1, 2, 3 or 4, and |
| p | is 1, 2, 3, 4 or 5. |

7. A pharmaceutically active ingredient comprising a compound of the formula I according to claim 1 or a physiologically acceptable salt or solvate thereof.

8. An integrin inhibitor comprising a compound of the formula I according to claim 1, or a physiologically acceptable salt or solvate thereof.

9. A pharmaceutical composition comprising at least one compound of the formula I according to claim 1 and/or a physiologically acceptable salt or solvate thereof and a pharmaceutically acceptable carrier.

10. A process for preparing a pharmaceutical composition comprising combining an effective amount of a compound according to claim 1 and/or a physiologically acceptable salt or solvate thereof with a pharmaceutically acceptable carrier.

11. A method for treating thromboses, cardiacinfarction, coronary heart disease, arteriosclerosis, inflammation, tumours, osteoporosis, infections, rheumatic arthritis, diabetic retinopathy or restenosis after angioplasty, comprising administering an effect amount of a compound according to claim 1 or a physiologically acceptable salt or solvate thereof to a patient in need thereof.

12. A compound according to claim 1, wherein Pol is a Wang resin or a polystyrene.

13. A compound according to claim 1, wherein Pol is a Rink amide resin.

14. A compound according to claim 1, wherein A is methyl or ethyl.

15. A compound according to claim 1, wherein Ar is phenyl.

16. A compound according to claim 1, wherein Het is pyridin-2-yl.

17. A compound according to claim 1, wherein:

| | |
|---|---|
| R¹ | is OR, |
| R | is H or A, |
| B | is H, |
| X | is O, |
| Y | is —N(R⁵)R⁴, |
| R⁴ | is Het, |

| | |
|---|---|
| R⁵ in —N(R⁵)R⁴ | is H, |
| m | is 2 or 3, and |
| n | is 1. |

18. A compound of the formula I

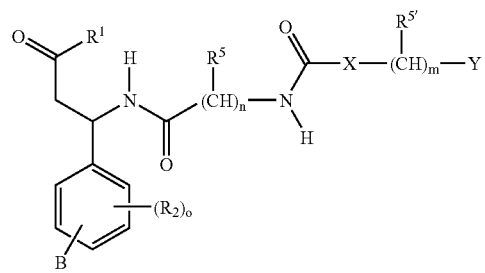

wherein

| | |
|---|---|
| X | is O or NR⁵, |
| Y | is —N(R⁵)R⁴, —C(=NR⁷)—NHR⁷ or —C(=NR⁹)—NHR⁷, |
| B | is H or |
| R | is H, A, cycloalkyl, Ar, arylalkyl or Pol, |
| R¹ | is OR or N(R)₂, |
| R² and R³ | each is, independently of one another, H, A, Hal, NO₂, OR, N(R)₂, CN, CO—R, SO₃R, SO₂R, NH—C(O)A or SR, |
| R⁴ | is H, R⁷, —C(=NR⁷)—NHR⁷, —C(=NR⁹)—NHR⁷, —C(=CH—NO₂)—NHR⁷ or Het, |
| R⁵ and R⁵' | each is, independently of one another, H or A, |
| R⁶ | is Hal or NO₂, |
| R⁷ | is H, —C(O)R⁸, —C(O)—Ar, R⁸, COOR⁸, COO—(CH₂)ₒ—Ar, SO₂—Ar, SO₂R⁸ or SO₂-Het, |
| R⁸ | is A or cycloalkyl, |
| R⁹ | is CN or NO₂, |
| A | is alkyl having from 1 to 8 carbon atoms, where the alkyl groups may be monosubstituted or polysubstituted by R⁶ and/or their alkyl carbon chain may be interrupted by —O—, |
| Ar | is phenyl, naphthyl, anthryl or biphenylyl, each of which is unsubstituted or monosubstituted, disubstituted or trisubstituted by A, OH, OA, CN, NO₂ or Hal, |
| cycloalkyl | is cycloalkyl having from 3 to 15 carbon atoms, |
| Hal | is F, Cl, Br or I, |
| Het | is a saturated, partially unsaturated or fully unsaturated monocyclic or bicyclic heterocyclic radical having from 5 to 10 ring members, where 1 or 2 N and/or 1 or 2 S or O atoms may be present, and the heterocyclic radical may be monosubstituted or disubstituted by =O, A, NO₂, NHCOA or NHA, |
| Pol | is a solid phase with no terminal functional group, |
| n and m | each is, independently of one another, 1, 2, 3, 4, 5 or 6, |
| o | is 1, 2, 3 or 4, and |
| p | is 1, 2, 3, 4 or 5, |

* * * * *

UNITED STATES PATENT AND TRADEMARK OFFICE
CERTIFICATE OF CORRECTION

PATENT NO.         : 7,135,587 B2
APPLICATION NO. : 10/450855
DATED              : November 14, 2006
INVENTOR(S)       : Wolfgang Staehle It is certified that error appears in the above-identified patent and that said Letters Patent is hereby corrected as shown below:

Column 30, line 28, insert -- or a physiologically acceptable salt or solvate thereof. --
Column 31, line 67, reads "$R_2$" should read -- $R^2$ --
Column 32, line 29, reads "converting, the" should read -- converting the --

Signed and Sealed this

Thirty-first Day of July, 2007

JON W. DUDAS
*Director of the United States Patent and Trademark Office*